(12) United States Patent
Ullrich, Jr. et al.

(10) Patent No.: US 8,585,766 B2
(45) Date of Patent: *Nov. 19, 2013

(54) ENDPLATE-PRESERVING SPINAL IMPLANT WITH AN INTEGRATION PLATE HAVING DURABLE CONNECTORS

(75) Inventors: Peter F. Ullrich, Jr., Neenah, WI (US); Chad J. Patterson, Port Washington, WI (US); Michelle B. Gallagher, Menomonee Falls, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/484,528

(22) Filed: May 31, 2012

(65) Prior Publication Data

US 2012/0245694 A1    Sep. 27, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)

(52) U.S. Cl.
USPC ..................... 623/17.16; 623/17.11

(58) Field of Classification Search
USPC ............................ 623/17.11–17.16
See application file for complete search history.

(56) References Cited

U.S. PATENT DOCUMENTS

| | | |
|---|---|---|
| 661,089 A | 11/1900 | Tanner |
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |

(Continued)

FOREIGN PATENT DOCUMENTS

| | | |
|---|---|---|
| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Eduardo C Robert
*Assistant Examiner* — Julianna N Harvey
(74) *Attorney, Agent, or Firm* — Stradley Ronon Stevens & Young, LLP

(57) ABSTRACT

An interbody spinal implant including a body having a top surface, a bottom surface, opposing lateral sides, opposing anterior and posterior portions, a substantially hollow center, and single vertical aperture, as well as an integration plate having a roughened surface topography on its top surface. The integration plate and implant body are joined together with a durable connection.

25 Claims, 33 Drawing Sheets

(56) References Cited

U.S. PATENT DOCUMENTS

| | | | |
|---|---|---|---|
| 5,571,188 A | 11/1996 | Ellingsen et al. | |
| 5,603,338 A | 2/1997 | Beaty | |
| 5,609,635 A | 3/1997 | Michelson | |
| 5,702,449 A * | 12/1997 | McKay | 623/17.16 |
| 5,755,798 A * | 5/1998 | Papavero et al. | 623/17.16 |
| 5,766,252 A | 6/1998 | Henry et al. | |
| 5,776,199 A | 7/1998 | Michelson | |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlaepfer et al. | |
| 6,080,158 A | 6/2000 | Lin | |
| 6,086,613 A * | 7/2000 | Camino et al. | 623/17.16 |
| 6,096,107 A * | 8/2000 | Caracostas et al. | 51/297 |
| 6,123,705 A | 9/2000 | Michelson | |
| 6,143,032 A | 11/2000 | Schafer et al. | |
| 6,176,882 B1 * | 1/2001 | Biedermann et al. | 623/17.15 |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 * | 2/2002 | Rabbe et al. | 623/17.11 |
| 6,350,283 B1 | 2/2002 | Michelson | |
| 6,375,681 B1 * | 4/2002 | Truscott | 623/17.11 |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,432,140 B1 | 8/2002 | Lin | |
| 6,436,102 B1 | 8/2002 | Ralph et al. | |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 * | 5/2003 | Moumene et al. | 623/17.11 |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Lie et al. | |
| 7,128,760 B2 | 10/2006 | Michelson | |
| 7,137,997 B2 | 11/2006 | Paul | |
| 7,144,428 B2 | 12/2006 | Anitua | |
| 7,166,129 B2 | 1/2007 | Michelson | |
| 7,169,183 B2 | 1/2007 | Liu et al. | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,062,304 B2 | 11/2011 | Blain et al. | |
| 8,100,955 B2 | 1/2012 | Blain et al. | |
| 8,142,355 B2 | 3/2012 | Blain et al. | |
| 8,172,854 B2 | 5/2012 | Blain et al. | |
| 8,262,737 B2 | 9/2012 | Bagga et al. | |
| 2001/0014826 A1 * | 8/2001 | Biedermann et al. | 623/17.11 |
| 2001/0016777 A1 | 8/2001 | Biscup | |
| 2001/0039464 A1 | 11/2001 | Ricci et al. | |
| 2001/0047208 A1 | 11/2001 | Michelson | |
| 2002/0049497 A1 | 4/2002 | Mason | |
| 2002/0087212 A1 | 7/2002 | James et al. | |
| 2002/0099443 A1 * | 7/2002 | Messerli et al. | 623/17.11 |
| 2002/0128716 A1 * | 9/2002 | Cohen et al. | 623/17.15 |
| 2002/0138142 A1 * | 9/2002 | Castro et al. | 623/17.11 |
| 2002/0161443 A1 * | 10/2002 | Michelson | 623/17.11 |
| 2002/0173854 A1 | 11/2002 | Amrich | |
| 2002/0188294 A1 | 12/2002 | Couture et al. | |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0125739 A1 | 7/2003 | Bagga et al. | |
| 2003/0153975 A1 | 8/2003 | Byrd, III et al. | |
| 2003/0176925 A1 * | 9/2003 | Paponneau | 623/17.16 |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 * | 10/2003 | Berry et al. | 623/17.11 |
| 2004/0117019 A1 | 6/2004 | Trieu et al. | |
| 2004/0117020 A1 | 6/2004 | Frey et al. | |
| 2004/0122518 A1 | 6/2004 | Rhoda | |
| 2004/0127993 A1 | 7/2004 | Kast et al. | |
| 2004/0153154 A1 | 8/2004 | Dinkelacker | |
| 2004/0153160 A1 * | 8/2004 | Carrasco | 623/17.15 |
| 2004/0162616 A1 | 8/2004 | Simonton et al. | |
| 2004/0167632 A1 | 8/2004 | Wen et al. | |

(56) References Cited

U.S. PATENT DOCUMENTS

| | | |
|---|---|---|
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1* | 2/2005 | Webb et al. ............... 623/17.11 |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0255414 A1* | 11/2007 | Melkent et al. ............ 623/17.16 |
| 2007/0260320 A1 | 11/2007 | Peterman et al. |
| 2007/0270827 A1* | 11/2007 | Lim et al. ................... 606/61 |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0004705 A1* | 1/2008 | Rogeau et al. ............. 623/17.16 |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2009/0005784 A1 | 1/2009 | Blain et al. |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2011/0040301 A1 | 2/2011 | Blain et al. |
| 2011/0082503 A1 | 4/2011 | Blain |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1* | 7/2012 | Bertele et al. ............... 623/17.16 |
| 2012/0232664 A1 | 9/2012 | Ullrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2 386 274 A1 | 11/2011 |
| JP | 19968010276 | 1/1996 |
| JP | 2001170092 | 6/2001 |
| WO | 9706753 | 2/1997 |
| WO | WO 98/01091 | 1/1998 |
| WO | 0128469 | 4/2001 |
| WO | 0170144 | 9/2001 |
| WO | 0195838 | 12/2001 |
| WO | WO 2004/041131 | 5/2004 |
| WO | 2006081843 | 8/2006 |
| WO | 2006116306 | 11/2006 |
| WO | 2006119088 | 11/2006 |
| WO | WO 2006/121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011 for EP 06 75 9086.

Supplementary Partial European Search Report issued Aug. 19, 2011. For EP 06 75 9086.

(56) References Cited

OTHER PUBLICATIONS

Variola, et al., "Nanoscale surface modifications of medically relevant metals: state-of-the art and prespectives", Nanoscale, 2011, 3, 335-353.
Wennerberg, et al., "Spontaneously formed nanostructures on titanium surfaces", Clin. Oral Impl. Res., 2012, 1-7.
Wennerberg, A., et al., "Effects of titanium surface topography on bone integration: a systematic review", Clin. Oral Impl. Res., 20 (Suppl. 4), 2009, pp. 172-184.
Pending U.S. Appl. No. 13/286,813 of Chad J. Patterson, et al. filed Nov. 1, 2011.
Pending U.S. Appl. No. 13/826,304 of Peter F. Ullrich, Jr., et al. filed Mar. 14, 2013.
Pending U.S. Appl. No. 13/713,417 of Chad J. Patterson, et al. filed Dec. 13, 2012.
Pending U.S. Appl. No. 13/784,144 of Peter F. Ullrich, Jr., et al. filed Mar. 4, 2013.

* cited by examiner

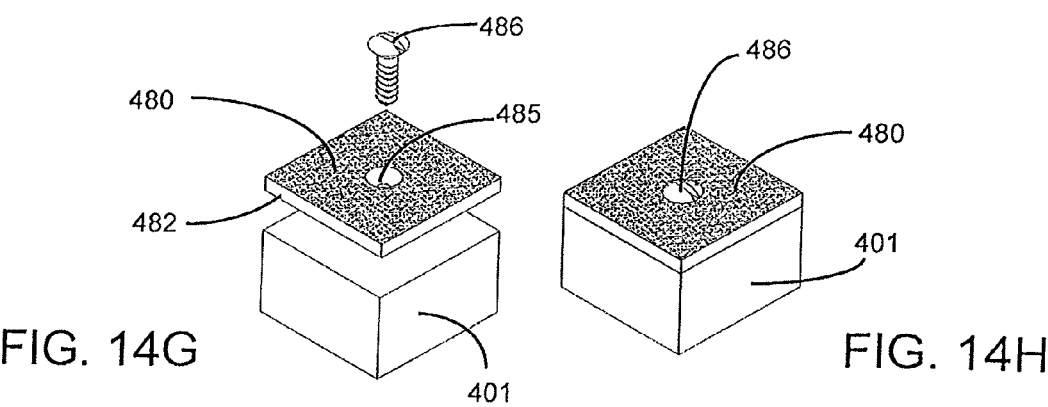
FIG. 14G  FIG. 14H
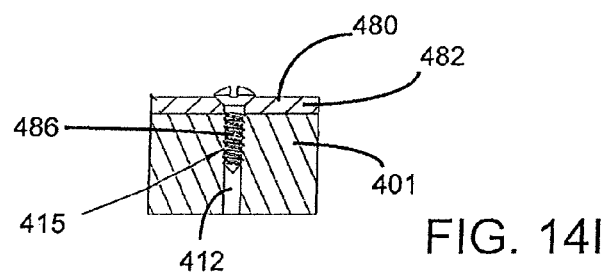
FIG. 14I
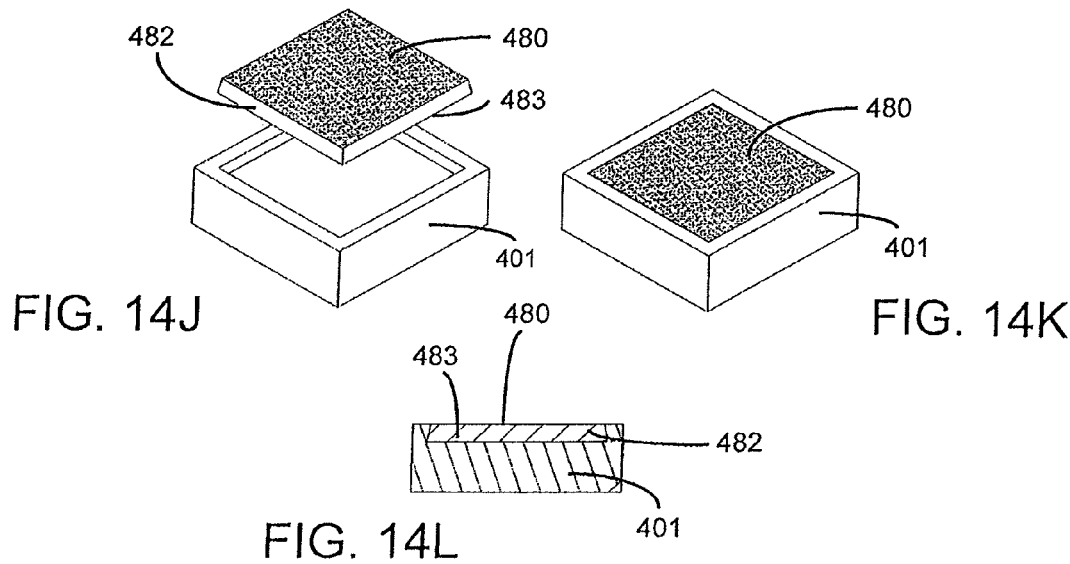
FIG. 14J  FIG. 14K
FIG. 14L

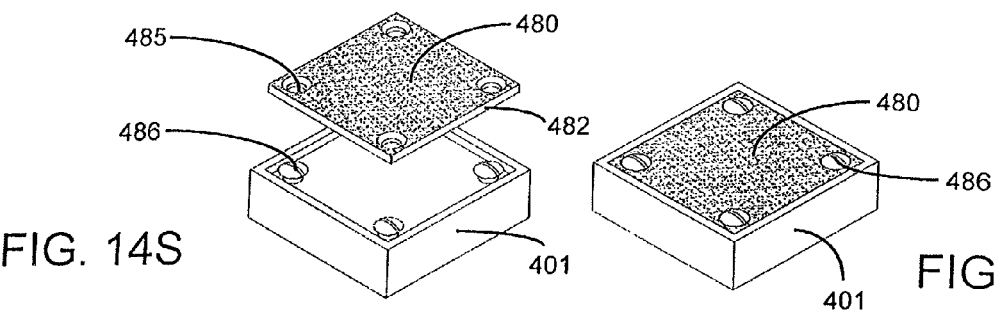
FIG. 14S  FIG. 14T
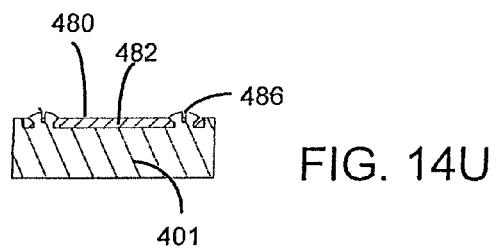
FIG. 14U
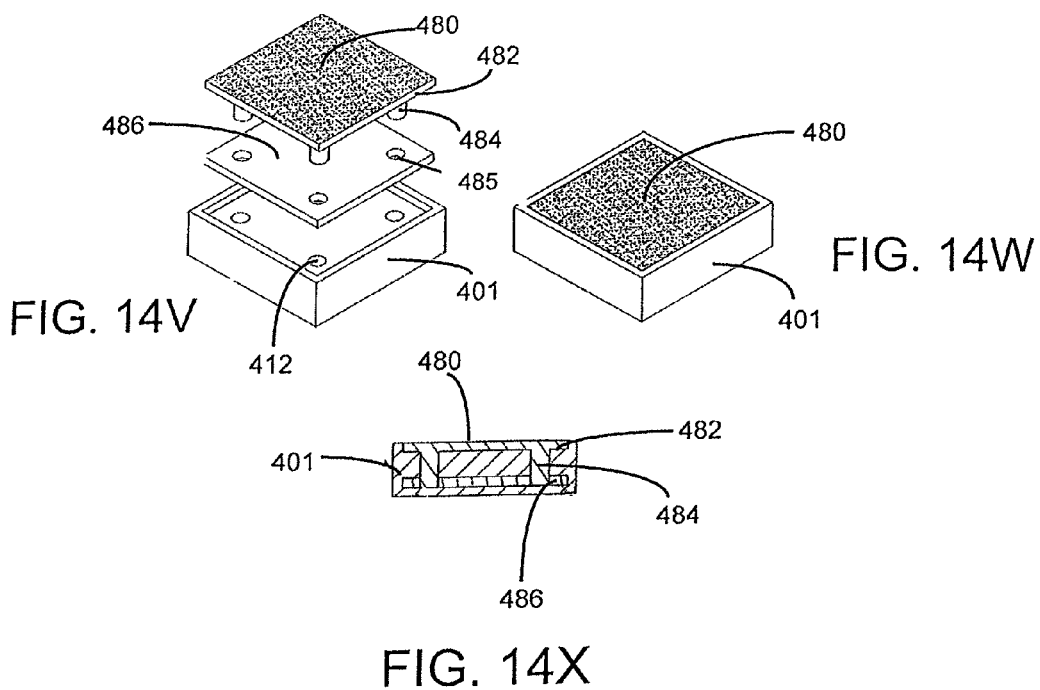
FIG. 14V  FIG. 14W
FIG. 14X

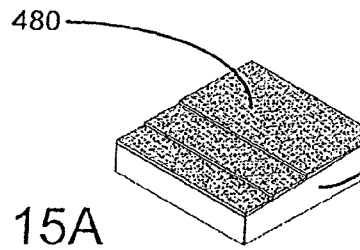
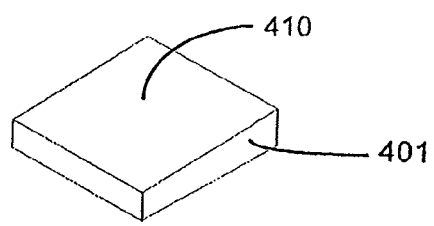
FIG. 15A  FIG. 15B
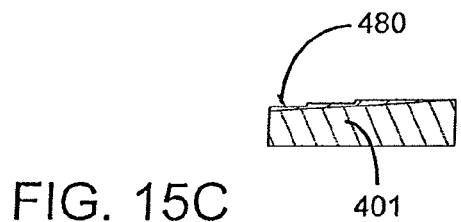
FIG. 15C
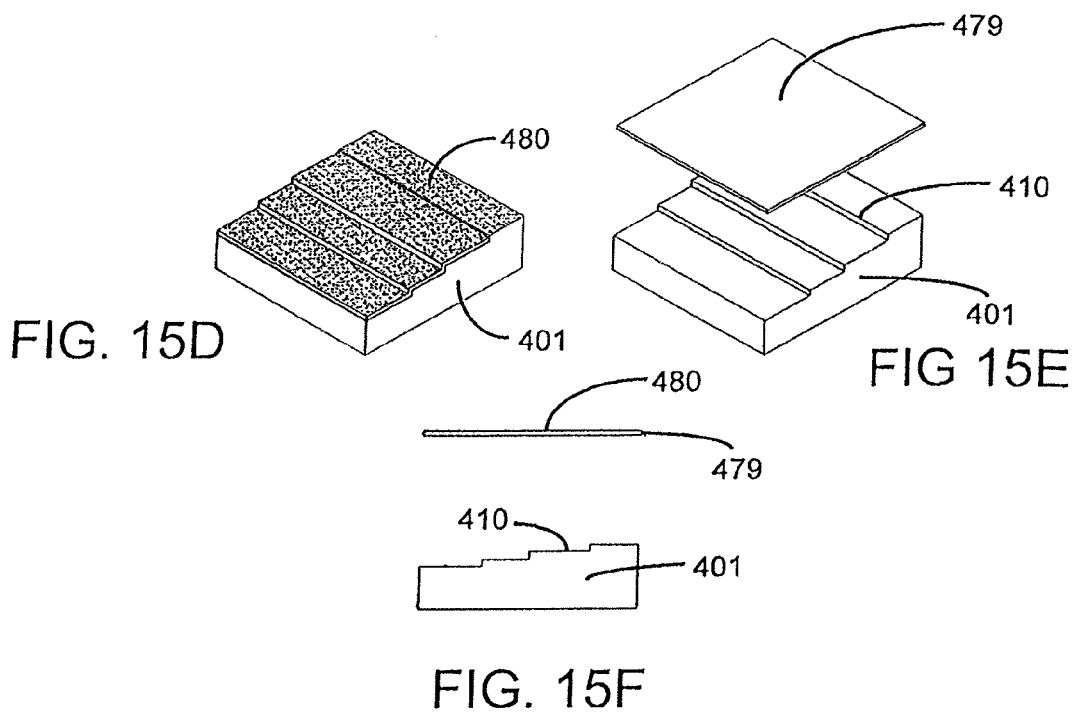
FIG. 15D  FIG. 15E
FIG. 15F

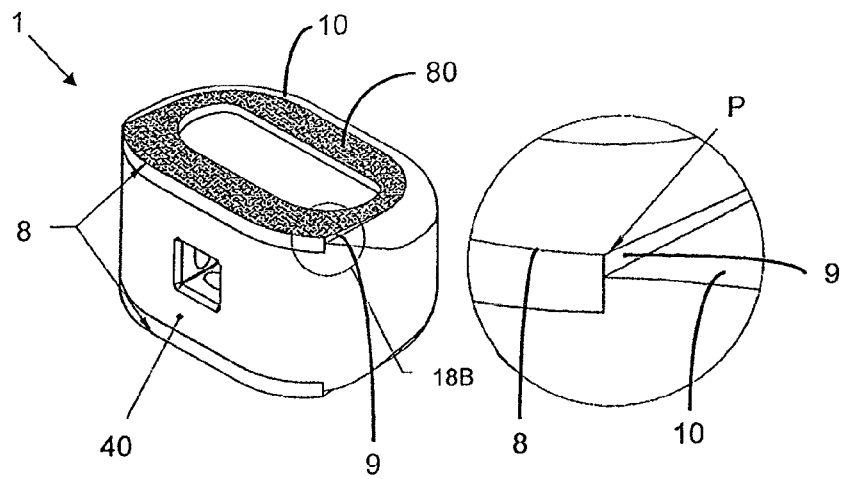
FIG. 18A
FIG. 18B
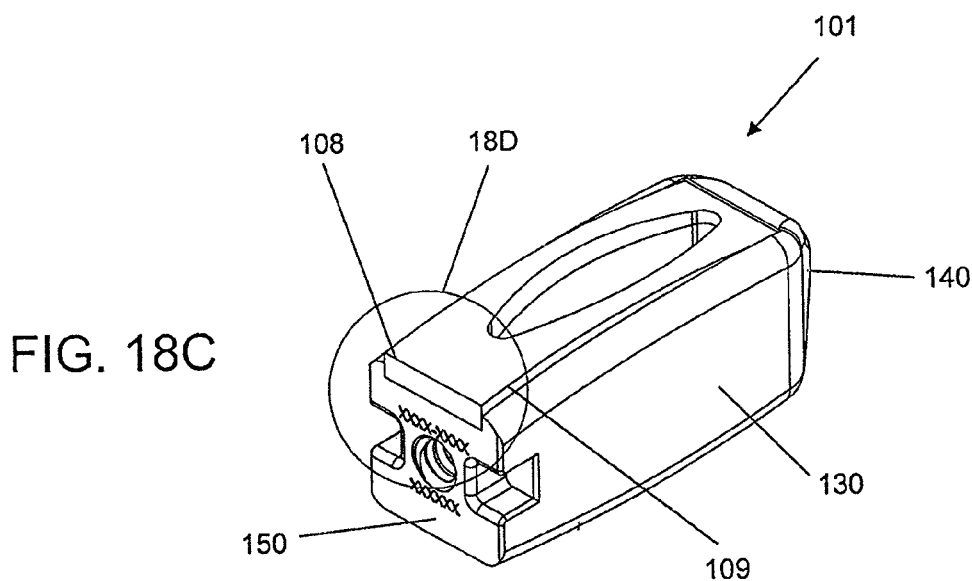
FIG. 18C
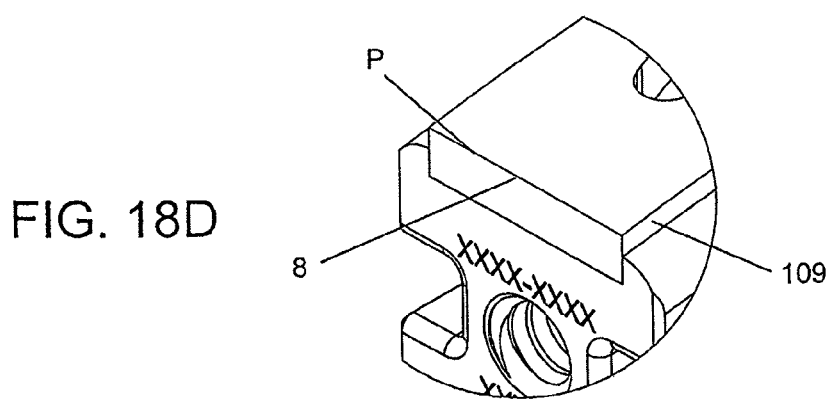
FIG. 18D

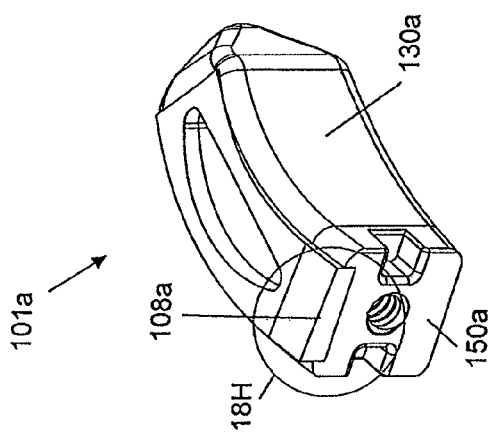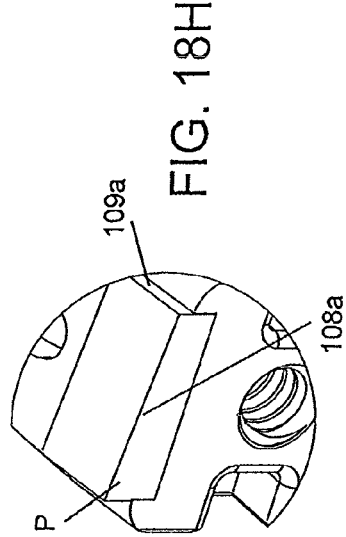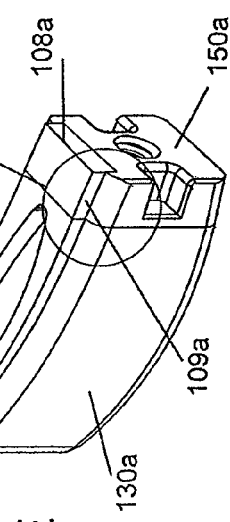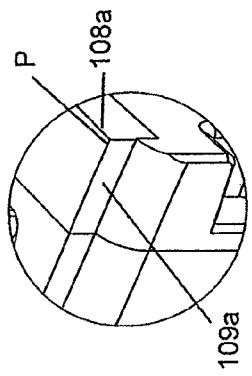

ENDPLATE-PRESERVING SPINAL IMPLANT WITH AN INTEGRATION PLATE HAVING DURABLE CONNECTORS

CROSS REFERENCE TO RELATED APPLICATIONS

This application is a continuation-in-part of U.S. patent application Ser. No. 12/151,198, filed on May 5, 2008, and pending, which is a continuation-in-part of U.S. patent application Ser. No. 11/123,359, filed on May 6, 2005, and issued as U.S. Pat. No. 7,662,186. The contents of both prior applications are incorporated by reference in this document, in their entirety and for all purposes.

FIELD OF THE INVENTION

The invention relates generally to interbody spinal implants and methods of using such implants and, more particularly, to an implant including an integration plate having a roughened surface topography, whereby the integration plate is affixed to the implant body by way of a durable connection established between a connector on the implant body and a reciprocal connector on the integration plate.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Several interbody implant systems have been introduced to facilitate interbody fusion. Traditional threaded implants involve at least two cylindrical bodies, each typically packed with bone graft material, surgically placed on opposite sides of the mid-sagittal plane through pre-tapped holes within the intervertebral disc space. This location is not the preferable seating position for an implant system, however, because only a relatively small portion of the vertebral endplate is contacted by these cylindrical implants. Accordingly, these implant bodies will likely contact the softer cancellous bone rather than the stronger cortical bone, or apophyseal rim, of the vertebral endplate. The seating of these threaded cylindrical implants may also compromise biomechanical integrity by reducing the area in which to distribute mechanical forces, thus increasing the apparent stress experienced by both the implant and vertebrae. Still further, a substantial risk of implant subsidence (defined as sinking or settling) into the softer cancellous bone of the vertebral body may arise from such improper seating.

In contrast, open ring-shaped cage implant systems are generally shaped to mimic the anatomical contour of the vertebral body. Traditional ring-shaped cages are generally comprised of allograft bone material, however, harvested from the human femur. Such allograft bone material restricts the usable size and shape of the resultant implant. For example, many of these femoral ring-shaped cages generally have a medial-lateral width of less than 25 mm. Therefore, these cages may not be of a sufficient size to contact the strong cortical bone, or apophyseal rim, of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Still further, other traditional non-allograft ring-shaped cage systems may be size-limited due to varied and complex supplemental implant instrumentation which may obstruct the disc space while requiring greater exposure of the operating space. These supplemental implant instrumentation systems also generally increase the instrument load upon the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Nevertheless, traditional implantation practices often do not preserve critical bone structures such as vertebral endplates during the surgical procedure. In some cases, the implant devices themselves necessitate removal of bone and were not designed or implanted with the intent to preserve critical bone structures during or after implantation.

In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

SUMMARY OF THE INVENTION

The invention is directed to interbody spinal implants and to methods of using such implants. The implants can be inserted, using methods of the invention, from a variety of vantages, including anterior, antero-lateral, and lateral implantation. The spinal implant is preferably adapted to be inserted into a prepared disc space via a procedure which does not destroy the vertebral end-plates, or contacts the vertebral end-plates only peripherally, allowing the intact vertebral end-plates to deflect like a diaphragm under axial compressive loads generated due to physiologic activities and pressurize the bone graft material disposed inside the spinal implant.

An implant preferably comprises a body and at least one integration plate, which are joined together. The body preferably comprises a top surface, a bottom surface, opposing lateral sides, opposing anterior and posterior portions, a substantially hollow center, and a single vertical aperture extending from the top surface to the bottom surface. The vertical aperture has a size and shape for maximizing the surface area of the top surface and the bottom surface available proximate the anterior and posterior portions while maximizing both radiographic visualization and access to the substantially hollow center, defines a transverse rim with a varying width or thickness, and has a maximum width at its center between the opposing lateral sides. The anterior portion of the body or the posterior portion of the body may comprise an opening for engaging a delivery device, facilitating delivery of bone graft material to the substantially hollow center, enhancing visibility of the implant, or providing access to bone graft material. In some embodiments, at least a portion of the top surface and/or the bottom surface of the body is recessed to a depth suitable to accommodate the thickness of the integration plate.

The integration plate comprises a top surface, a bottom surface, opposing lateral sides, opposing anterior and posterior portions, and a single vertical aperture extending from the top surface to the bottom surface. Preferably, the vertical aperture aligns with the single vertical aperture of the body, defines a transverse rim with a varying width or thickness, and has a maximum width at its center. The top surface of the integration plate comprises a roughened surface topography adapted to grip bone and inhibit migration of the implant.

The top surface and/or bottom surface of the implant comprises a connector, and the bottom surface of the integration plate comprises a reciprocal connector. The connector and reciprocal connector may be joined together to affix the integration plate onto the implant.

In some aspects, the connector comprises a plurality of holes and the reciprocal connector comprises a plurality of posts inserted into the plurality of holes, and each of the posts may comprise a bore extending through it in a horizontal plane. A pin may be inserted into the bore to lock the post in the hole. In some aspects, the connector comprises an anchor plate comprising a plurality of holes, and the reciprocal connector comprises a plurality of posts inserted into the plurality of holes on the anchor plate. In some aspects, the reciprocal connector comprises one or more bores in the bottom surface of the integration plate, and the connector comprises one or more rods inserted into the one or more bores in the bottom surface of the integration plate. In some aspects, the reciprocal connector comprises a plurality of vertical bores extending through the integration plate, and the connector comprises a plurality of screws inserted into the plurality of vertical bores and into the top surface of the body or the bottom surface of the body. In some aspects, the reciprocal connector comprises a plurality of vertical bores extending through the integration plate, and the connector comprises a plurality of snap buttons inserted through the plurality of vertical bores. In some aspects, the reciprocal connector of the integration plate and the connector of the body each comprise compatibly shaped undercuts that form an interlocking joint when the reciprocal connector and the connector are joined together.

The invention also features an interbody spinal implant comprising a body having a top surface, a bottom surface, opposing lateral sides, opposing anterior and posterior portions, a substantially hollow center, and a single vertical aperture extending from the top surface to the bottom surface, having a size and shape for maximizing the surface area of the top surface and the bottom surface available proximate the anterior and posterior portions, defining a transverse rim with a varying width or thickness, and having a maximum width at its center. At least a portion of the top surface, and optionally at least a portion of the bottom surface, comprises a roughened surface topography adapted to grip bone and inhibit migration of the implant. The roughened surface topography comprises metal particles, metal fibers, metal powder, or combinations thereof affixed to the top surface, and optionally the bottom surface, of the implant. In alternative aspects, the interbody spinal implant comprises a body and an integration plate, and in such embodiments, the top surface of the integration plate comprises a roughened surface topography adapted to grip bone and inhibit migration of the implant, and the roughened surface topography comprises metal particles, metal fibers, metal powder, or combinations thereof affixed to the top surface of the integration plate.

The metal particles, metal fibers, metal powder, or combinations thereof may be affixed to the top surface and/or bottom surface of the implant, or to the top surface of the integration plate, with an adhesive. The metal particles, metal fibers, metal powder, or combinations thereof may be cold sprayed onto the top surface and/or bottom surface of the implant, or to the top surface of the integration plate. The metal particles, metal fibers, metal powder, or combinations thereof may be thermal sprayed onto the top surface and/or bottom surface of the implant, or to the top surface of the integration plate. In some aspects, the metal particles, metal fibers, metal powder, or combinations thereof are comprised on a foil backing and the foil backing is affixed to the top surface and/or bottom surface of the implant, or to the top surface of the integration plate.

In any implant, the substantially hollow portion of the body may contain a bone graft material adapted to facilitate the formation of a solid fusion column within the spine. The bone graft material may be cancellous autograft bone, allograft bone, demineralized bone matrix (DBM), porous synthetic bone graft substitute, bone morphogenic protein (BMP), or a combination thereof. The body may comprise a wall closing at least one of the opposing anterior and posterior portions of the body for containing the bone graft material.

The implant body and/or the integration plate may be fabricated from a metal. A preferred metal is titanium. The implant body may be fabricated from a non-metallic material, non-limiting examples of which include polyetherether-ketone, hedrocel, ultra-high molecular weight polyethylene, and combinations thereof. The implant body may be fabricated from both a metal and a non-metallic material, including a composite thereof. For example, a composite may be formed, in part, of titanium and, in part, of polyetherether-ketone, hedrocel, ultra-high molecular weight polyethylene, or combinations thereof.

The body and the integration plate are preferably compatibly shaped, such that the implant with the body and integration plate joined together may have a generally oval shape, a generally rectangular shape, a generally curved shape, or any other shape described or exemplified in this specification. Thus, for example, the body and the integration plate may be generally oval-shaped in transverse cross-section. The body and the integration plate may be generally rectangular-shaped in transverse cross-section. The body and the integration plate may be generally curved-shaped in transverse cross-section.

The implant may comprise a lordotic angle adapted to facilitate alignment of the spine. At least one of the anterior and posterior portions of the integration plate may comprise an anti-expulsion edge to resist pullout of the implant from the spine of a patient into which the implant has been implanted.

The invention also features systems that include such interbody spinal implants. The systems may comprise an implant and a distractor. The systems may further comprise a rasp. The systems may further comprise an implant holder capable of engaging an opening on the anterior portion of the spinal implant. The systems may further comprise a bone graft material, non-limiting examples of which include cancellous autograft bone, allograft bone, demineralized bone matrix (DBM), porous synthetic bone graft substitute, bone morphogenic protein (BMP), or a combination thereof.

It is to be understood that both the foregoing general description and the following detailed description are exemplary, but are not restrictive, of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures:

FIG. 14G shows an exploded view of a fastener connection suitable for mounting an integration plate onto an implant;

FIG. 14H shows the fastener connection illustrated in FIG. 14G with the components assembled;

FIG. 14I shows a cut-away view of the fastener connection illustrated in FIGS. 14G and 14H;

FIG. 14J shows an exploded view of an undercut retention connection suitable for mounting an integration plate onto an implant;

FIG. 14K shows the undercut retention connection illustrated in FIG. 14J with the components assembled;

FIG. 14L shows a cut-away view of the undercut retention connection illustrated in FIGS. 14J and 14K;

FIG. 14S shows an exploded view of a snap-fit connection suitable for mounting an integration plate onto an implant;

FIG. 14T shows the snap-fit connection illustrated in FIG. 14S with the components assembled;

FIG. 14U shows a cut-away view of the snap-fit connection illustrated in FIGS. 14S and 14T;

FIG. 14V shows an exploded view of an internal molded connection suitable for mounting an integration plate onto an implant;

FIG. 14W shows the internal molded connection illustrated in FIG. 14V with the components assembled;

FIG. 14X shows a cut-away view of the internal molded connection illustrated in FIGS. 14V and 14W;

FIG. 15A shows an example of a roughened topography capable of being created by coating a material onto the surface of an implant;

FIG. 15B shows a flat implant surface capable of receiving a coated roughened topography;

FIG. 15C shows a cut-away view of the coated roughened topography illustrated in FIG. 15A;

FIG. 15D shows an example of a roughened topography capable of being created by pressing a flexible foil onto the surface of an implant;

FIG. 15E shows an exploded view of the flexible foil and implant surface;

FIG. 15F shows an exploded side view of the flexible foil and implant illustrated in FIG. 15E;

FIG. 18A shows an oval-shaped implant with a protruding anti-expulsion edge;

FIG. 18B shows a close-up view of the protruding anti-expulsion edge of the implant illustrated in FIG. 18A;

FIG. 18C shows a rectangular-shaped implant with a protruding anti-expulsion edge oriented toward the posterior portion;

FIG. 18D shows a close-up view of the protruding anti-expulsion edge of the implant illustrated in FIG. 18C;

FIG. 18E shows a perspective view of a curved-shaped implant with a protruding anti-expulsion edge oriented toward the posterior portion;

FIG. 18F shows a close-up view of the protruding anti-expulsion edge of the implant perspective illustrated in FIG. 18E;

FIG. 18G shows another perspective view of the implant illustrated in FIG. 18E;

FIG. 18H shows a close-up view of the protruding anti-expulsion edge of the implant illustrated in FIG. 18G;

DETAILED DESCRIPTION OF THE INVENTION

Certain embodiments of the invention may be especially suited for placement between adjacent human vertebral bodies. The implants of the invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the invention, allow for improved visualization of implant seating and fusion assessment. Interbody spinal implants, as now taught, may also facilitate osteointegration with the surrounding living bone.

Anterior interbody spinal implants in accordance with certain aspects of the invention can be preferably made of a durable material such as stainless steel, stainless steel alloy, titanium, or titanium alloy, but can also be made of other durable materials such as, but not limited to, polymeric, ceramic, and composite materials. For example, certain embodiments of the invention may be comprised of a biocompatible, polymeric matrix reinforced with bioactive fillers, fibers, or both. Certain embodiments of the invention may be comprised of urethane dimethacrylate (DUDMA)/tri-ethylene glycol dimethacrylate (TEDGMA) blended resin and a plurality of fillers and fibers including bioactive fillers and E-glass fibers. Durable materials may also consist of any number of pure metals, metal alloys, or both. Titanium and its alloys are generally preferred for certain embodiments of the invention due to their acceptable, and desirable, strength and biocompatibility. In this manner, certain embodiments of the present interbody spinal implant may have improved structural integrity and may better resist fracture during implantation by impact. Interbody spinal implants, as now taught, may therefore be used as a distractor during implantation.

Figure 1A:
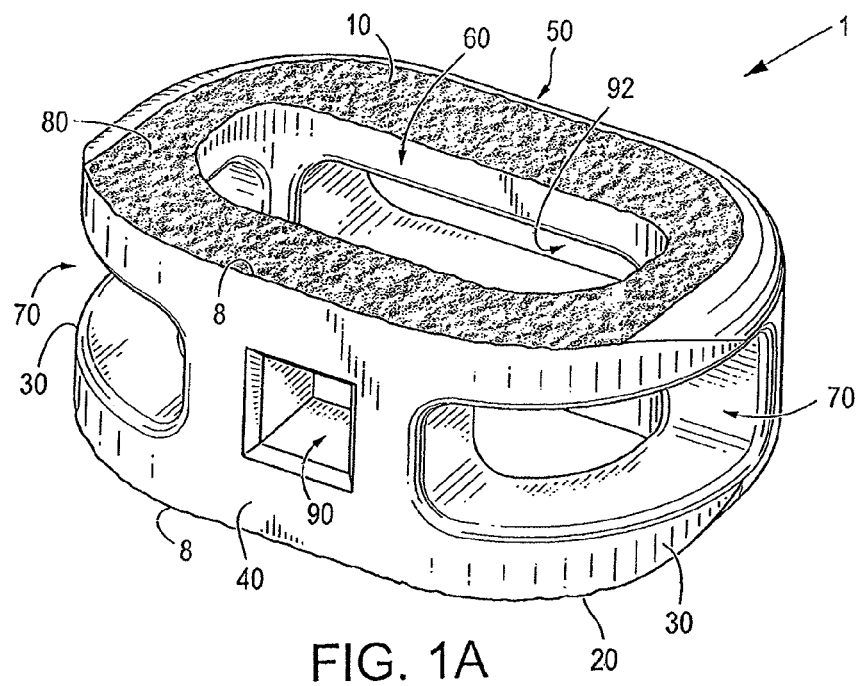
FIG. 1A shows a perspective view of an embodiment of the interbody spinal implant having a generally oval shape and roughened surface topography on the top surface.
Figure 1B:
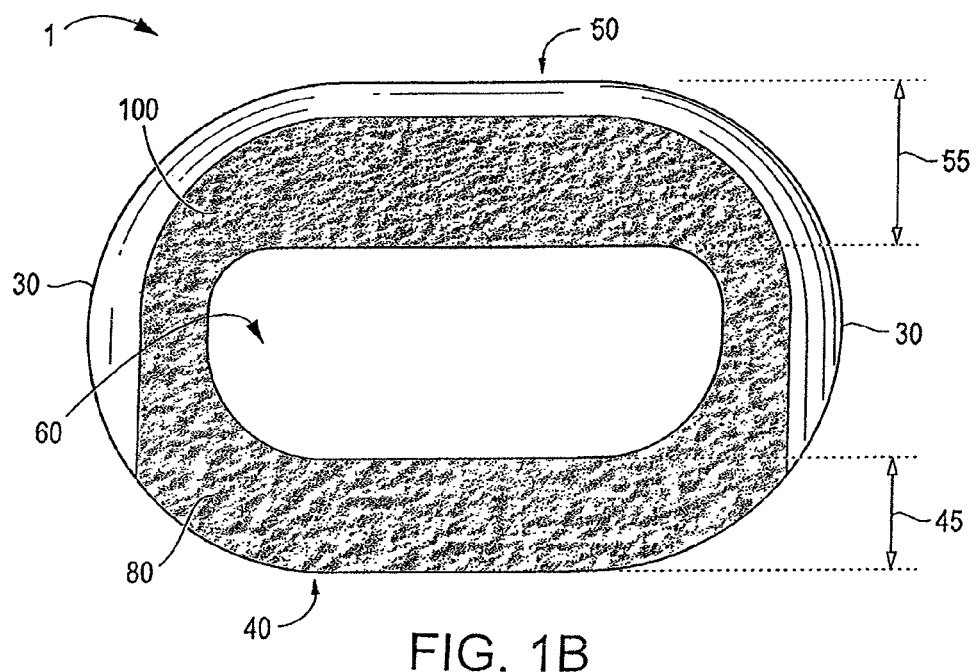
FIG. 1B shows a top view of the first embodiment of the interbody spinal implant illustrated in FIG. 1A.

Referring now to the drawing, in which like reference numbers refer to like elements throughout the various figures that comprise the drawing, FIG. 1 shows a perspective view of a first embodiment of the interbody spinal implant 1 especially well adapted for use in an ALIF procedure.

The interbody spinal implant 1 includes a body having a top surface 10, a bottom surface 20, opposing lateral sides 30, and opposing anterior 40 and posterior 50 portions. One or both of the top surface 10 and the bottom surface 20 has a roughened topography 80. The roughened topography 80, however, is distinct from the teeth provided on the surfaces of some conventional devices.

In some aspects, the interbody spinal implant 1 is substantially hollow and has a generally oval-shaped transverse cross-sectional area with smooth, rounded, or both smooth and rounded lateral sides 30 and posterior-lateral corners 52. A substantially hollow implant 1 includes an implant 1 having at least about 33% of the interior volume of the implant 1 vacant. The implant 1 includes at least one vertical aperture 60 that extends the entire height of the implant body. The vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40. Some studies have challenged the characterization of the posterior endplate bone as weaker.

It is generally believed that the surface of an implant determines its ultimate ability to integrate into the surrounding living bone. Without being limited to any particular theory or mechanism of action, it is believed that the cumulative effects of at least implant composition, implant surface energy, and implant surface roughness play a major role in the biological response to, and osteointegration of, an implant device. Thus, implant fixation may depend, at least in part, on the attachment and proliferation of osteoblasts and like-functioning cells upon the implant surface. Still further, it appears that these cells attach more readily to relatively rough surfaces rather than smooth surfaces. In this manner, a surface may be bioactive due to its ability to facilitate cellular attachment and osteointegration. The surface roughened topography 80 may better promote the osteointegration of the implant 1. The surface roughened topography 80 may also better grip the vertebral endplate surfaces and inhibit implant migration of the implant 1 upon placement and seating in a patient.

Accordingly, the implant 1 further includes the roughened topography 80 on at least a portion of its top 10 and bottom 20 surfaces for gripping adjacent bone and inhibiting migration of the implant 1. FIG. 1 shows roughened topography 80 on an embodiment of the implant 1.

The roughened topography 80 may be obtained through a variety of techniques including, without limitation, chemical etching, shot peening, plasma etching, laser etching, or abrasive blasting (such as sand or grit blasting). In at least one embodiment, the interbody spinal implant 1 may be comprised of titanium, or a titanium alloy, having the surface roughened topography 80. The surfaces of the implant 1 are preferably bioactive.

In a preferred embodiment of the invention, the roughened topography 80 is obtained via the repetitive masking and chemical or electrochemical milling processes described in U.S. Pat. No. 5,258,098; No. 5,507,815; No. 5,922,029; and No. 6,193,762. Each of these patents is incorporated in this document by reference. Where the invention employs chemical etching, the surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features.

By way of example, an etchant mixture of nitric acid ($HNO_3$) and hydrofluoric (HF) acid may be repeatedly applied to a titanium surface to produce an average etch depth of about 0.53 mm. Interbody spinal implants 1, in accordance with some preferred embodiments of the invention, may be comprised of titanium, or a titanium alloy, having an average surface roughness of about 100 μm. Surface roughness may be measured using a laser profilometer or other standard instrumentation.

In another example, chemical modification of the titanium implant surfaces can be achieved using HF and a combination of hydrochloric acid and sulfuric acid ($HCl/H_2SO_4$). In a dual acid etching process, the first exposure is to HF and the second is to $HCl/H_2SO_4$. Chemical acid etching alone of the titanium implant surface has the potential to greatly enhance osteointegration without adding particulate matter (e.g., hydroxyapatite) or embedding surface contaminants (e.g., grit particles).

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim. The implant 1 may also include an anti-expulsion edge 8 as described in more detail below.

As illustrated in FIG. 1, the implant 1 has an opening 90 in the anterior portion 40. In one embodiment the posterior portion 50 has a similarly shaped opening 90. In some aspects, only the anterior portion 40 has the opening 90 while the posterior portion 50 has an alternative opening 92 (which may have a size and shape different from the opening 90).

The opening 90 has a number of functions. One function is to facilitate manipulation of the implant 1 by the caretaker. Thus, the caretaker may insert a surgical tool into the opening 90 and, through the engagement between the surgical tool and the opening 90, manipulate the implant 1. The opening 90 may be threaded to enhance the engagement.

The implant 1 may further include at least one transverse aperture 70 that extends the entire transverse length of the implant body. The at least one transverse aperture 70 may provide improved visibility of the implant 1 during surgical procedures to ensure proper implant placement and seating, and may also improve post-operative assessment of implant fusion. Still further, the substantially hollow area defined by the implant 1 may be filled with cancellous autograft bone, allograft bone, DBM, porous synthetic bone graft substitute, BMP, or combinations of these materials (collectively, bone graft materials), to facilitate the formation of a solid fusion column within the spine of a patient.

Certain embodiments of the invention are particularly suited for use during interbody spinal implant procedures (or vertebral body replacement procedures) and may act as a final distractor during implantation, thus minimizing the instrument load upon the surgeon. For example, in such a surgical procedure, the spine may first be exposed via an anterior approach and the center of the disc space identified. The disc space is then initially prepared for implant insertion by removing vertebral cartilage. Soft tissue and residual cartilage may then also be removed from the vertebral endplates.

Vertebral distraction may be performed using trials of various-sized embodiments of the interbody spinal implant 1. The determinatively sized interbody implant 1 may then be inserted in the prepared disc space for final placement. The distraction procedure and final insertion may also be performed under fluoroscopic guidance. The substantially hollow area within the implant body may optionally be filled, at least partially, with bone fusion-enabling materials such as, without limitation, cancellous autograft bone, allograft bone, DBM, porous synthetic bone graft substitute, BMP, or combinations of those materials. Such bone fusion-enabling material may be delivered to the interior of the interbody spinal implant 1 using a delivery device mated with the opening 90 in the anterior portion 40 of the implant 1. The interbody spinal implant 1 may be generally larger than those currently known in the art, and therefore have a correspondingly larger hollow area which may deliver larger volumes of fusion-enabling bone graft material. The bone graft material may be delivered such that it fills the full volume, or less than the full volume, of the implant interior and surrounding disc space appropriately.

Figure 2:
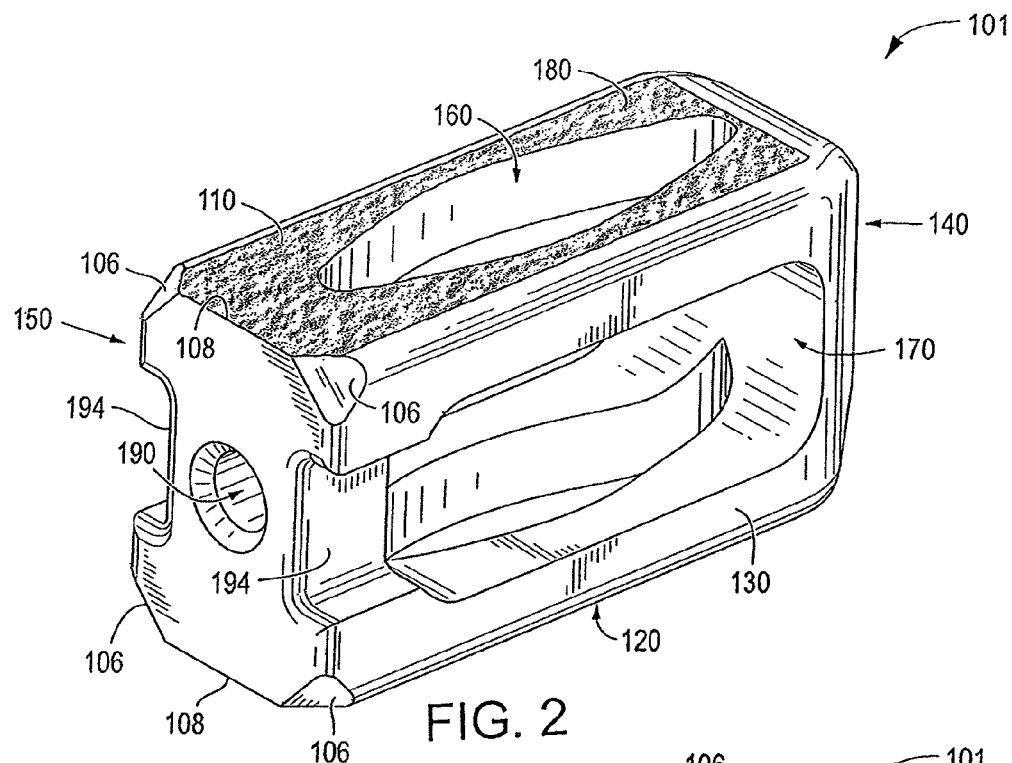
FIG. 2 shows a perspective view from the front of another embodiment of the interbody spinal implant according to the invention.
Figure 3:
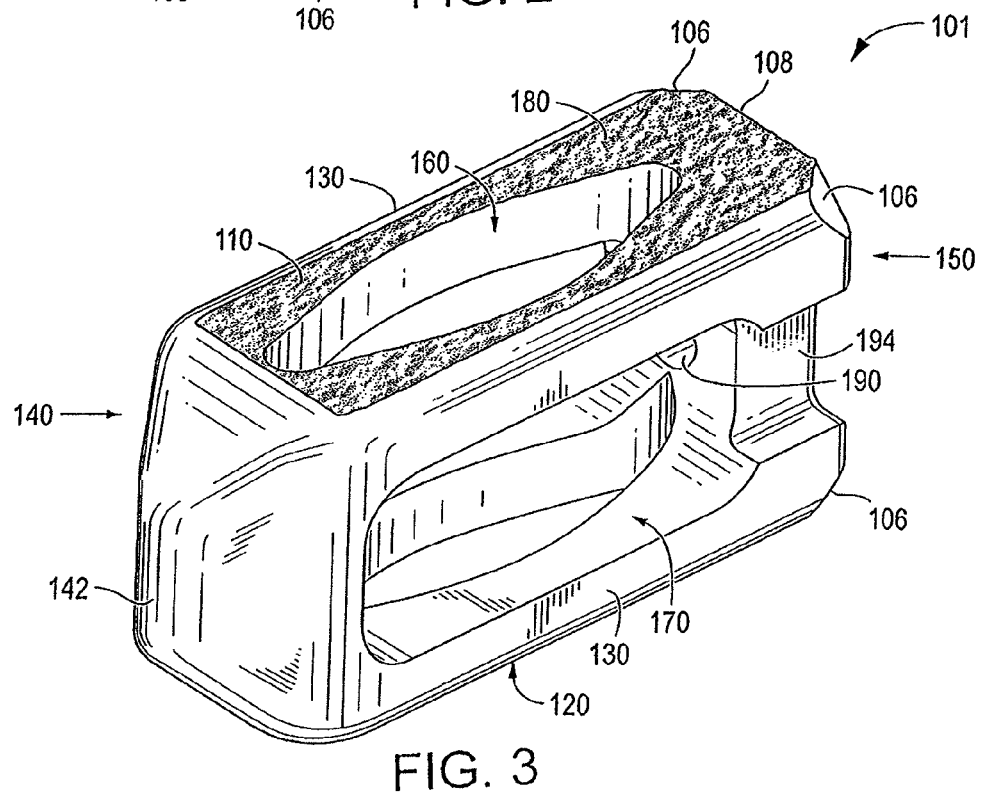
FIG. 3 shows a perspective view from the rear of the embodiment of the interbody spinal implant illustrated in FIG. 2.

As noted above, FIG. 1 shows a perspective view of one embodiment of the invention, the interbody spinal implant 1, which is especially well adapted for use in an ALIF procedure. Other embodiments of the invention are better suited for PLIF, TLIF, or cervical fusion procedures. Specifically, FIGS. 2 and 3 show perspective views, from the front and rear, respectively, of an embodiment of an interbody spinal implant 101 especially well adapted for use in a PLIF procedure. The interbody spinal implant 101 includes a body having a top surface 110, a bottom surface 120, opposing lateral sides 130, and opposing anterior 140 and posterior 150 portions. One or both of the top surface 110 and the bottom surface 120 has a roughened topography 180 for gripping adjacent bone and inhibiting migration of the implant 101.

Certain embodiments of the interbody spinal implant 101 are substantially hollow and have a generally rectangular shape with smooth, rounded, or both smooth and rounded lateral sides and anterior-lateral corners. As best shown in FIG. 3, the anterior portion 140 may have a tapered nose 142 to facilitate insertion of the implant 101. To further facilitate insertion, the implant 101 has chamfers 106 at the corners of its posterior portion 150. The chamfers 106 prevent the implant 101 from catching upon insertion, risking potential damage such as severed nerves, while still permitting the implant 101 to have an anti-expulsion edge 108.

The implant 101 includes at least one vertical aperture 160 that extends the entire height of the implant body. The vertical aperture 160 further defines a transverse rim 200. The size and shape of the vertical aperture 160 are carefully chosen to achieve a preferable design tradeoff for the particular application envisioned for the implant 101. Specifically, the vertical aperture 160 seeks to maximize the surface area of the top surface 110 and the bottom surface 120 available proximate the anterior 140 and posterior 150 portions while maximizing both radiographic visualization and access to the bone graft material toward the center of the top 110 and bottom 120 surfaces. Thus, the size and shape of the vertical aperture 160 are predetermined by the application to which the implant 101 will be used.

In the particular example shown in FIGS. 2 and 3, the width of the implant 101 between the two lateral sides 130 is approximately 9 mm. The shape of the vertical aperture 160 approximates, in cross section, that of an American football. The center of the vertical aperture 160, which defines the maximum width of the vertical aperture 160, is about 5 mm. Thus, the rim thickness 200 on either side of the vertical aperture 160 adjacent the center of the vertical aperture 160 is about 2 mm. These dimensions permit ample engagement between the bone graft material contained within the implant 101 and bone.

The vertical aperture 160 tapers from its center to its ends along a longitudinal distance of about 7.75 mm (thus, the total length of the vertical aperture 160 is about 15.5 mm). This shape leaves intact much of the rim thickness 200 in the areas around the ends of the vertical aperture 160. These areas may allow for better stress sharing between the implant 101 and the adjacent vertebral endplates. Thus, the transverse rim 200 has a generally large surface area and contacts the vertebral endplate.

As illustrated in FIG. 2, the implant 101 has an opening 190 in the posterior portion 150. The opening 190 has a number of functions. One function is to facilitate manipulation of the implant 101 by the caretaker. Thus, the caretaker may insert a surgical tool into the opening 190 and, through the engagement between the surgical tool and the opening 190, manipulate the implant 101. The opening 190 may be threaded to enhance the engagement.

The implant 101 may also have an Implant Holding Feature (IHF) 194 instead of or in addition to the opening 190. As illustrated in FIG. 2, the IHF 194 is located proximate the opening 190 in the posterior portion 150. In this particular example, the IHF 194 is a U-shaped notch. Like the opening 190, the IHF 194 has a number of functions, one of which is to facilitate manipulation of the implant 101 by the caretaker. Other functions of the opening 190 and the IHF 194 are to increase visibility of the implant 101 during surgical procedures and to enhance engagement between bone graft material and adjacent bone.

The implant 101 may further include at least one transverse aperture 170. Like the vertical aperture 160, the size and shape of the transverse aperture 170 are carefully chosen (and predetermined) to achieve a preferable design tradeoff for the particular application envisioned for the implant 101. Specifically, the transverse aperture 170 should have minimal dimensions to maximize the strength and structural integrity of the implant 101. On the other hand, the transverse aperture 70 should have maximum dimensions to (a) improve the visibility of the implant 101 during surgical procedures to ensure proper implant placement and seating, and to improve post-operative assessment of implant fusion, and (b) to facilitate engagement between bone graft material and adjacent bone. The substantially hollow area defined by the implant 101 may be filled with bone graft materials to facilitate the formation of a solid fusion column within the spine of a patient.

As shown in FIGS. 2 and 3, the transverse aperture 170 extends the entire transverse length of the implant body and nearly the entire height of the implant body. Thus, the size and shape of the transverse aperture 170 approach the maximum possible dimensions for the transverse aperture 170.

The transverse aperture 170 may be broken into two, separate sections by an intermediate wall 172. The section of the transverse aperture 170 proximate the IHF 194 is substantially rectangular in shape; the other section of the transverse aperture 170 has the shape of a curved arch. Other shapes and dimensions are suitable for the transverse aperture 170. In particular, all edges of the transverse aperture 170 may be rounded, smooth, or both. The intermediate wall 172 may be made of the same material as the remainder of the implant 101 (e.g., metal), or it may be made of another material (e.g., PEEK) to form a composite implant 101. The intermediate wall 172 may offer one or more of several advantages, including reinforcement of the implant 101 and improved bone graft containment.

The embodiment of the invention illustrated in FIGS. 2 and 3 is especially well suited for a PLIF surgical procedure. TLIF surgery is done through the posterior (rear) part of the spine and is essentially like an extended PLIF procedure. The TLIF procedure was developed in response to some of the technical problems encountered with a PLIF procedure. The main difference between the two spine fusion procedures is that the TLIF approach to the disc space is expanded by removing one entire facet joint; a PLIF procedure is usually done on both sides by only taking a portion of each of the paired facet joints.

By removing the entire facet joint, visualization into the disc space is improved and more disc material can be removed. Such removal should also provide for less nerve retraction. Because one entire facet is removed, the TLIF procedure is only done on one side: removing the facet joints on both sides of the spine would result in too much instability. With increased visualization and room for dissection, one or both of a larger implant and more bone graft can be used in the TLIF procedure. Theoretically, these advantages can allow the spine surgeon to distract the disc space more and realign the spine better (re-establish the normal lumbar lordosis).

Although the TLIF procedure offers some improvements over a PLIF procedure, the anterior approach in most cases still provides the best visualization, most surface area for healing, and the best reduction of any of the approaches to the disc space. These advantages must be weighed, however, against the increased morbidity (e.g., unwanted aftereffects and postoperative discomfort) of a second incision. Probably the biggest determinate in how the disc space is approached is the comfort level that the spine surgeon has with an anterior approach for the spine fusion surgery. Not all spine surgeons are comfortable with operating around the great vessels (aorta and vena cava) or have access to a skilled vascular surgeon to help them with the approach. Therefore, choosing one of the posterior approaches for the spine fusion surgery is often a more practical solution.

Figure 4:
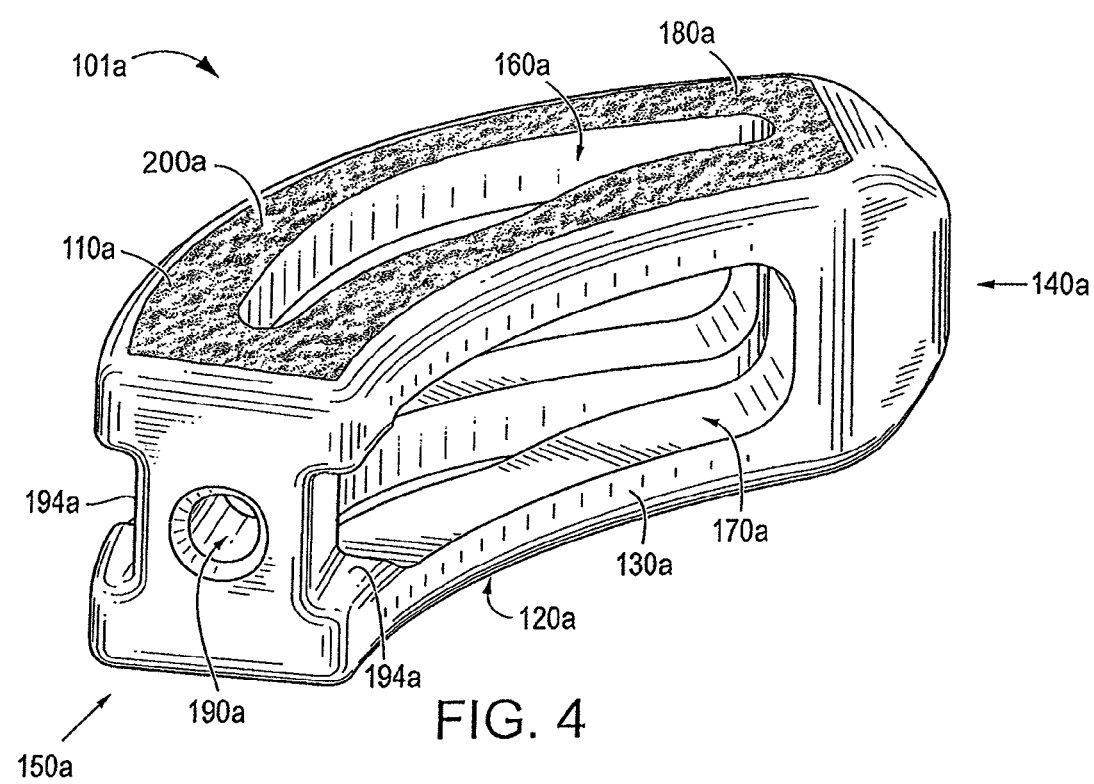
FIG. 4 shows a perspective view from the front of yet another embodiment of the interbody spinal implant according to the invention.
Figure 5:
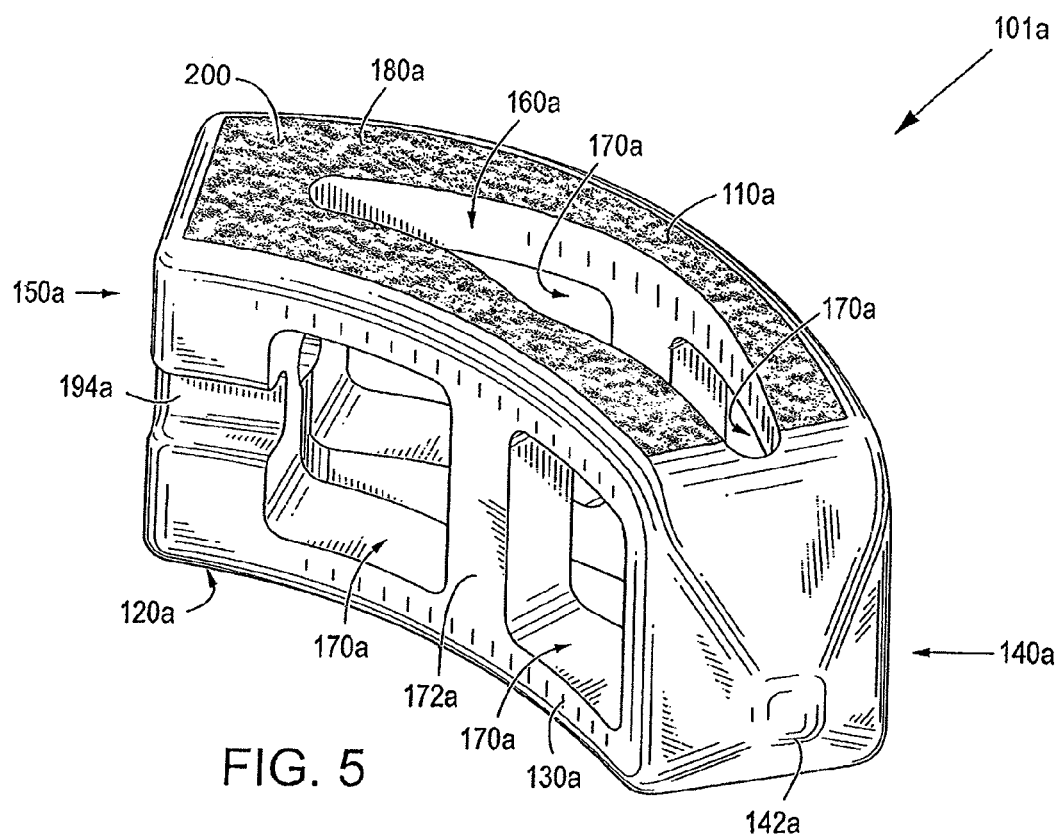
FIG. 5 shows a perspective view from the rear of the embodiment of the interbody spinal implant illustrated in FIG. 4 highlighting an alternative transverse aperture.

The embodiment of the invention illustrated in FIGS. 4 and 5 is especially well suited when the spine surgeon elects a TLIF procedure. Many of the features of the implant 101a illustrated in FIGS. 4 and 5 are the same as those of the implant 101 illustrated in FIGS. 2 and 3. Therefore, these features are given the same reference numbers, with the addition of the letter "a," and are not described further.

There are several differences, however, between the two embodiments. For example, unlike the substantially rectangular shape of the implant 101, the implant 101a has a curved shape. Further, the chamfers 106 and anti-expulsion edge 108 of the implant 101 are replaced by curves or rounded edges for the implant 101a. Still further, the TLIF procedure often permits use of a larger implant 101a which, in turn, may affect the size and shape of the predetermined vertical aperture 160a.

The substantially constant 9 mm width of the transverse rim 200 of the implant 101 is replaced with a larger, curved transverse rim 200a. The width of the transverse rim 200a is 9 mm in the regions adjacent the anterior 140a and posterior 150a portions. That width gradually increases to 11 mm, however, near the center of the transverse rim 200a. The additional real estate provided by the transverse rim 200a (relative to the transverse rim 200) allows the shape of the vertical aperture 160a to change, in cross section, from approximating a football to approximating a boomerang. Maintaining the thickness of the transverse rim 200a on either side of the vertical aperture 160a adjacent the center of the vertical aperture 160a at about 2 mm, similar to the dimensions of the implant 101, the center of the vertical aperture 160a, which defines the maximum width of the vertical aperture 160a, is increased (from 5 mm for the implant 101) to about 7 mm.

The implant 101a may also have a lordotic angle to facilitate alignment. The lateral side 130a depicted at the top of the implant 101a is preferably generally greater in height than the opposing lateral side 130a. Therefore, the implant 101a may better compensate for the generally less supportive bone found in certain regions of the vertebral endplate.

As shown in FIG. 4, the transverse aperture 170a extends the entire transverse length of the implant body and nearly the entire height of the implant body. FIG. 5 highlights an alternative transverse aperture 170a. As illustrated in FIG. 5, the transverse aperture 170a is broken into two, separate sections by an intermediate wall 172a. Thus, the dimensions of the transverse aperture 170a shown in FIG. 5 are much smaller than those for the transverse aperture 170a shown in FIG. 4. The two sections of the alternative transverse aperture 170a are each illustrated as substantially rectangular in shape and extending nearly the entire height of the implant body; other sizes and shapes are possible for one or both sections of the alternative transverse aperture 170a.

The intermediate wall 172a may be made of the same material as the remainder of the implant 101a (e.g., metal), or it may be made of another material (e.g., PEEK) to form a composite implant 101a. It is also possible to extend the intermediate wall 172a, whether made of metal, PEEK, ultra-high molecular weight polyethylene (UHMWPE), or another material, to eliminate entirely the transverse aperture 170a. Given the reinforcement function of the intermediate wall 172a, the length of the vertical aperture 160a can be extended (as shown in FIG. 5) beyond the top surface 110a and into the anterior portion 140a of the implant 101a.

The top surface 110a of the implant 101a need not include the roughened topography 180a. This difference permits the implant 101a, at least for certain applications, to be made entirely of a non-metal material. Suitable materials of construction for the implant 101a of such a design (which would not be a composite) include PEEK, hedrocel, UHMWPE, other radiolucent soft plastics, and additional materials as would be known to an artisan.

The embodiments of the invention described above are best suited for one or more of the ALIF, PLIF, and TLIF surgical procedures. Another embodiment of the invention is better suited for cervical fusion procedures. This embodiment is illustrated in FIGS. 6 and 7 as the interbody spinal implant 201.

Because there is not a lot of disc material between the vertebral bodies in the cervical spine, the discs are usually not very large. The space available for the nerves is also not that great, however, which means that even a small cervical disc herniation may impinge on the nerve and cause significant pain. There is also less mechanical load on the discs in the cervical spine as opposed to the load that exists lower in the spine. Among others, these differences have ramifications for the design of the implant 201.

The implant 201 is generally smaller in size than the other implant embodiments. In addition, the lower mechanical load requirements imposed by the cervical application typically render a composite implant unnecessary. Therefore, the implant 201 is generally made entirely of metal (e.g., titanium) and devoid of other materials (e.g., PEEK).

Figure 6:
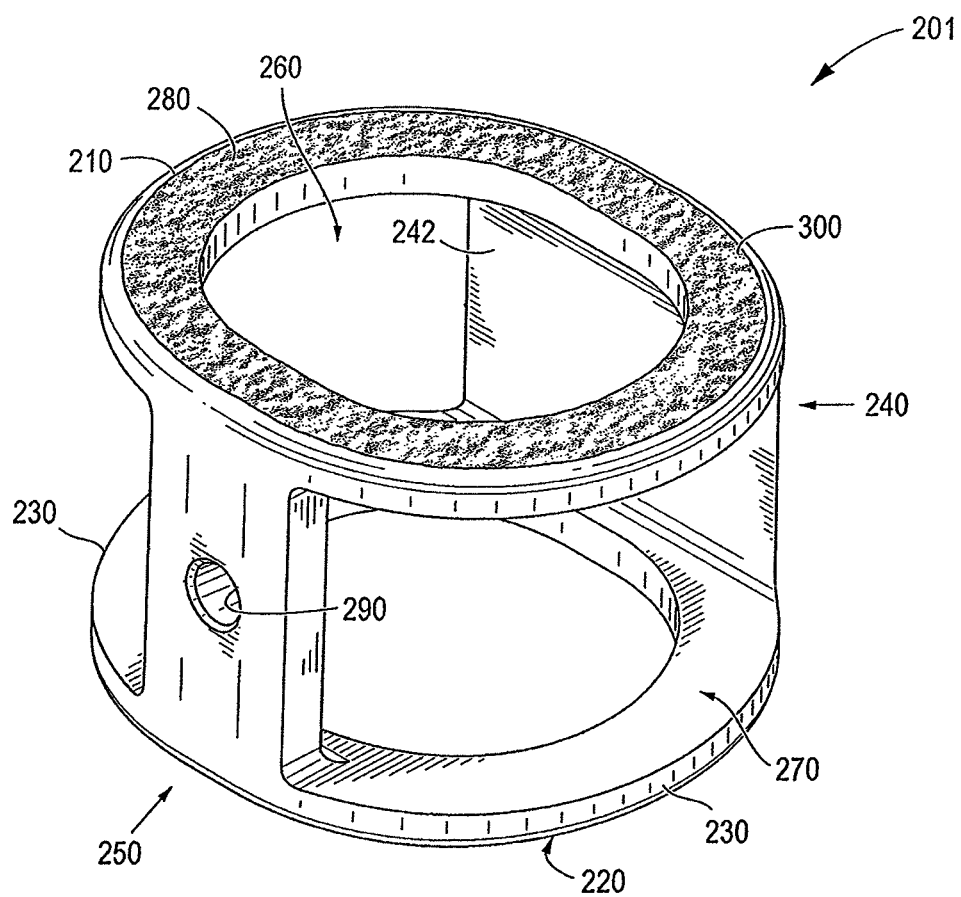
FIG. 6 shows a perspective view of another embodiment of the interbody spinal implant having a generally oval shape and being especially well adapted for use in a cervical spine surgical procedure.
Figure 7:
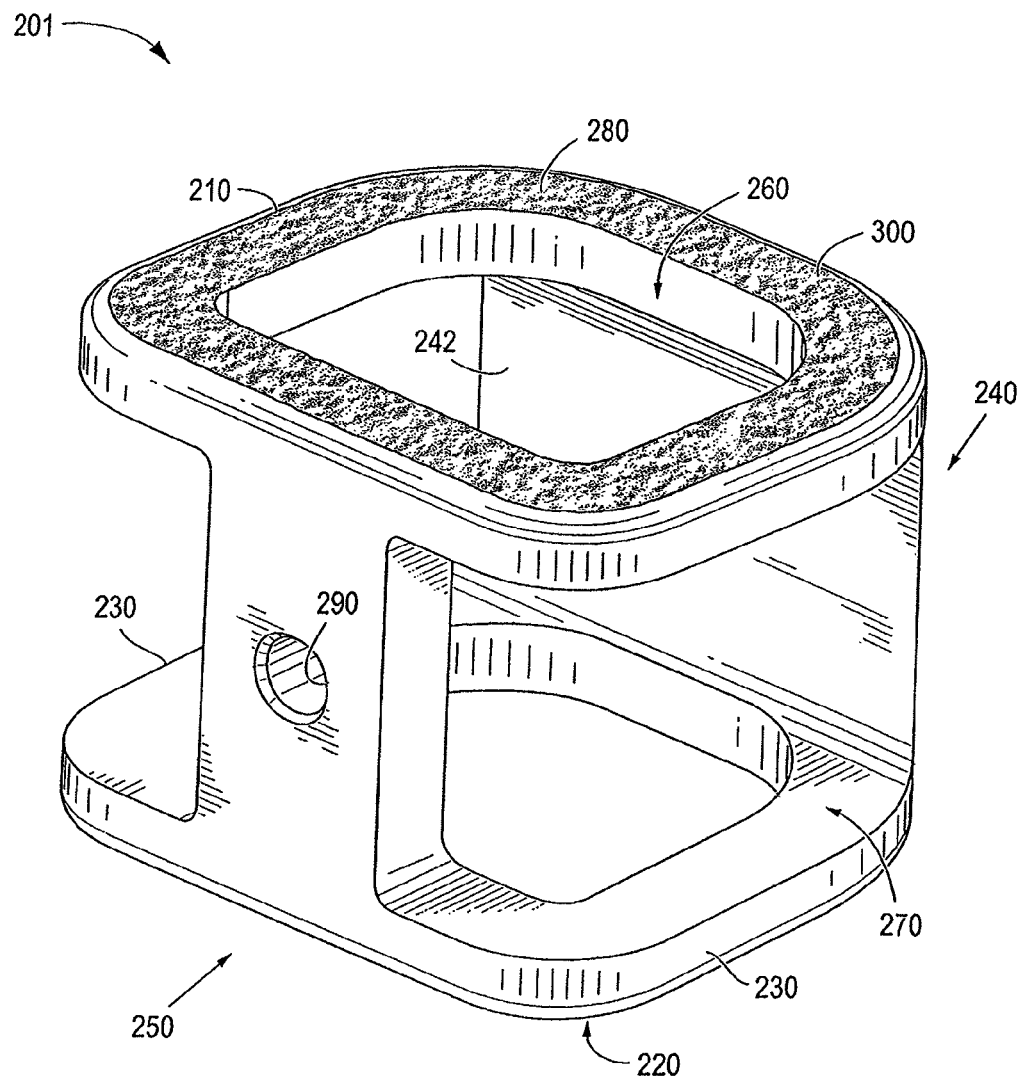
FIG. 7 shows a perspective view of an implant having a generally box shape.

With specific reference to FIG. 6, the implant 201 includes a body having a top surface 210, a bottom surface 220, opposing lateral sides 230, and opposing anterior 240 and posterior 250 portions. One or both of the top surface 210 and the bottom surface 220 has a roughened topography 280 for gripping adjacent bone and inhibiting migration of the implant 201. The implant 201 is substantially hollow and has a generally oval shape with smooth, rounded, or both smooth and rounded edges.

The implant 201 includes at least one vertical aperture 260 that extends the entire height of the implant body. The vertical aperture 260 further defines a transverse rim 300. The size and shape of the vertical aperture 260 are carefully chosen to achieve a preferable design tradeoff for the particular application envisioned for the implant 201. Specifically, the vertical aperture 260 seeks to maximize the surface area of the top surface 210 and the bottom surface 220, to allow for better stress sharing between the implant 201 and the adjacent vertebral endplates, while maximizing access to the bone graft material provided within the implant 201. Thus, the size and shape of the vertical aperture 260 are predetermined by the application.

As illustrated in FIG. 6, the implant 201 has an opening 290 in the posterior portion 250. The opening 290 has a number of functions. One function is to facilitate manipulation of the implant 201 by the caretaker. Thus, the caretaker may insert a surgical tool into the opening 290 and, through the engagement between the surgical tool and the opening 290, manipulate the implant 201. The opening 290 may be threaded to enhance the engagement.

The implant 201 may further include at least one transverse aperture 270. Like the vertical aperture 260, the size and shape of the transverse aperture 270 are carefully chosen (and predetermined) to achieve a preferable design tradeoff for the particular application envisioned for the implant 201. For example, as shown in FIG. 6, the transverse aperture 270 may extend the entire transverse length of the implant body and nearly the entire height of the implant body. Thus, the size and shape of the transverse aperture 270 approach the maximum possible dimensions for the transverse aperture 270.

As illustrated in FIG. 6, the implant 201 may be provided with a solid rear wall 242. The rear wall 242 extends the entire width of the implant body and nearly the entire height of the implant body. Thus, the rear wall 242 essentially closes the anterior portion 240 of the implant 201. The rear wall 242 may offer one or more of several advantages, including reinforcement of the implant 201 and improved bone graft containment. In the cervical application, it may be important to prevent bone graft material from entering the spinal canal.

Alternative shapes for the implant 201 are possible. As illustrated in FIG. 7, for example, the implant 201 may have a generally box shape which gives the implant 201 increased cortical bone coverage. Like the implant 201 shown in FIG. 6, the implant 201 shown in FIG. 7 has a curved transverse rim 300 in the area of the anterior portion 240. The shape of the posterior portion 250 of the implant 201 is substantially flat, however, and the shape of the transverse rim 300 in the area of the posterior portion 250 is substantially square. Thus, the posterior portion 250 provides a face that can receive impact from a tool, such as a surgical hammer, to force the implant 201 into position.

The implant 201 may also have a lordotic angle to facilitate alignment. As illustrated in FIGS. 6 and 7, the anterior portion 240 is preferably generally greater in height than the posterior portion 250. Therefore, the implant 201 may better compensate for the generally less supportive bone found in certain regions of the vertebral endplate. As an example, four degrees of lordosis may be built into the implant 201 to help restore balance to the spine.

Certain embodiments of the implant 1, 101, 101a, and 201 are generally shaped (i.e., made wide) to maximize contact with the apophyseal rim of the vertebral endplates. They are designed to be impacted between the endplates, with fixation to the endplates created by an interference fit and annular tension. Thus, the implants 1, 101, 101a, and 201 are shaped and sized to spare the vertebral endplates and leave intact the hoop stress of the endplates. A wide range of sizes are possible to capture the apophyseal rim, along with a broad width of the peripheral rim, especially in the posterior region. It is expected that such designs will lead to reduced subsidence. As much as seven degrees of lordosis (or more) may be built into the implants 1, 101, 101a, and 201 to help restore cervical balance.

When endplate-sparing spinal implant 1, 101, 101a, and 201 seats in the disc space against the apophyseal rim, it should still allow for deflection of the endplates like a diaphragm. This means that, regardless of the stiffness of the spinal implant 1, 101, 101a, and 201, the bone graft material inside the spinal implant 1, 101, 101a, and 201 receives load, leading to healthy fusion. The vertical load in the human spine is transferred though the peripheral cortex of the vertebral bodies. By implanting an apophyseal-supporting inter-body implant 1, 101, 101a, and 201, the natural biomechanics may be better preserved than for conventional devices. If this is true, the adjacent vertebral bodies should be better preserved by the implant 1, 101, 101a, and 201, hence reducing the risk of adjacent segment issues.

In addition, the dual-acid etched roughened topography 80, 180, 180a, and 280 of the top surface 30, 130, 130a, and 230 and the bottom surface 40, 140, 140a, and 240 along with the broad surface area of contact with the end-plates, is expected to yield a high pull-out force in comparison to conventional designs. As enhanced by the sharp edges 8 and 108, a pull-out strength of up to 3,000 nt may be expected. The roughened topography 80, 180, 180a, and 280 creates a biological bond with the end-plates over time, which should enhance the quality of fusion to the bone. Also, the in-growth starts to happen much earlier than the bony fusion. The center of the implant 1, 101, 101a, and 201 remains open to receive bone graft material and enhance fusion. Therefore, it is possible that patients might be able to achieve a full activity level sooner than for conventional designs.

The spinal implant 1, 101, 101a, and 201 according to the invention offers several advantages relative to conventional devices. Such conventional devices include, among others, ring-shaped cages made of allograft bone material, threaded titanium cages, and ring-shaped cages made of PEEK or carbon fiber.

Figure 9:
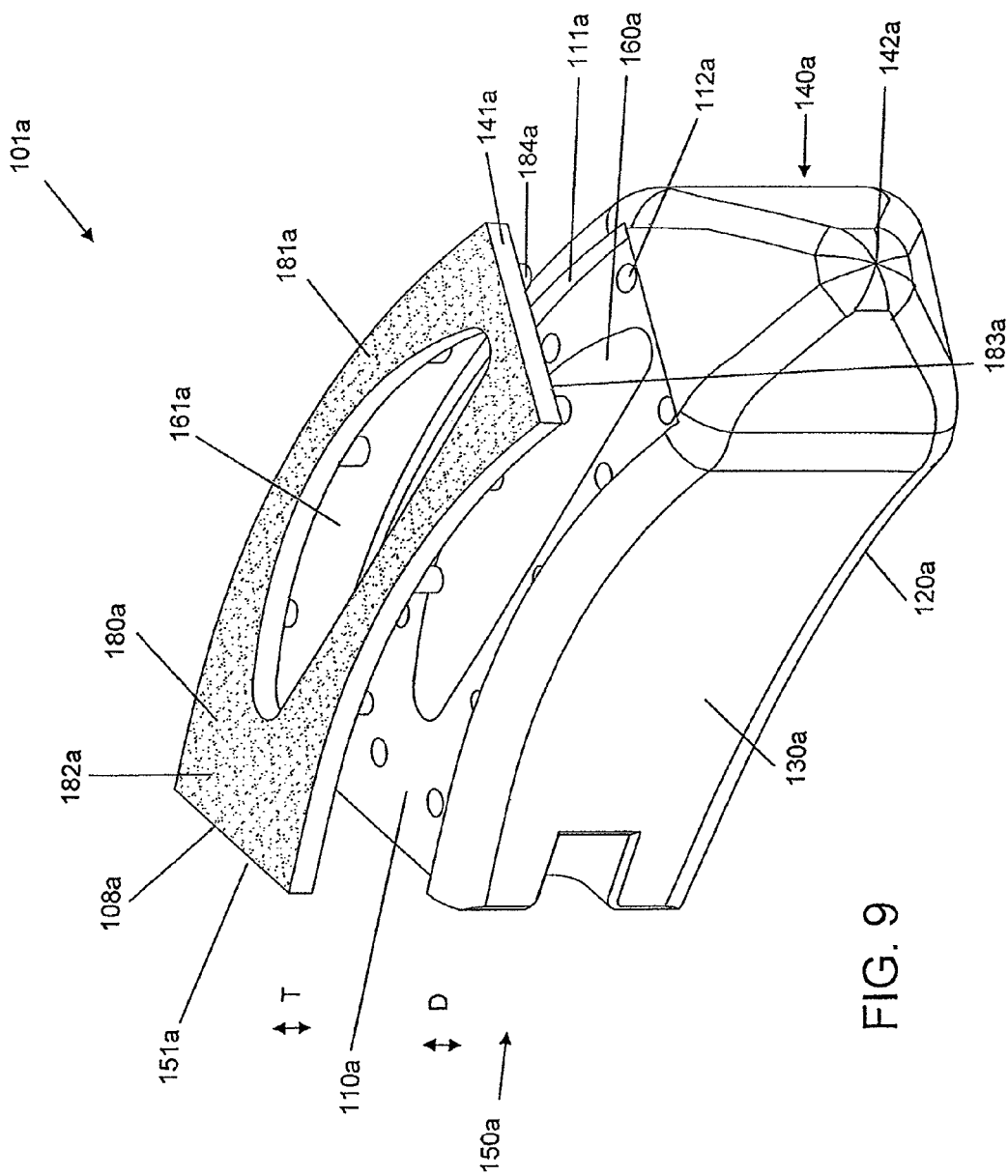
FIG. 9 shows an exploded view of a curved implant with an integration plate.
Figure 10:
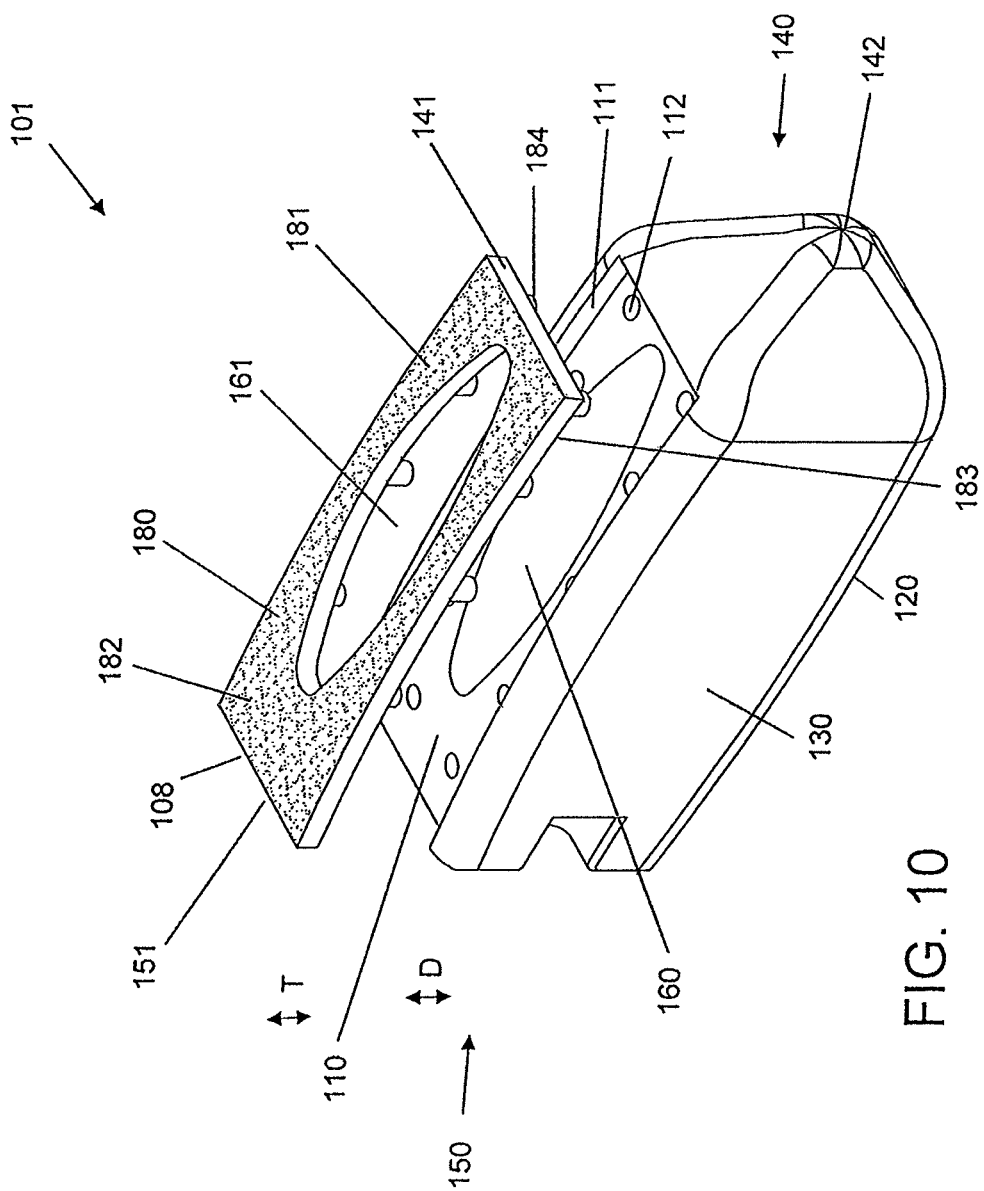
FIG. 10 shows an exploded view of a posterior implant with an integration plate.
Figure 11:
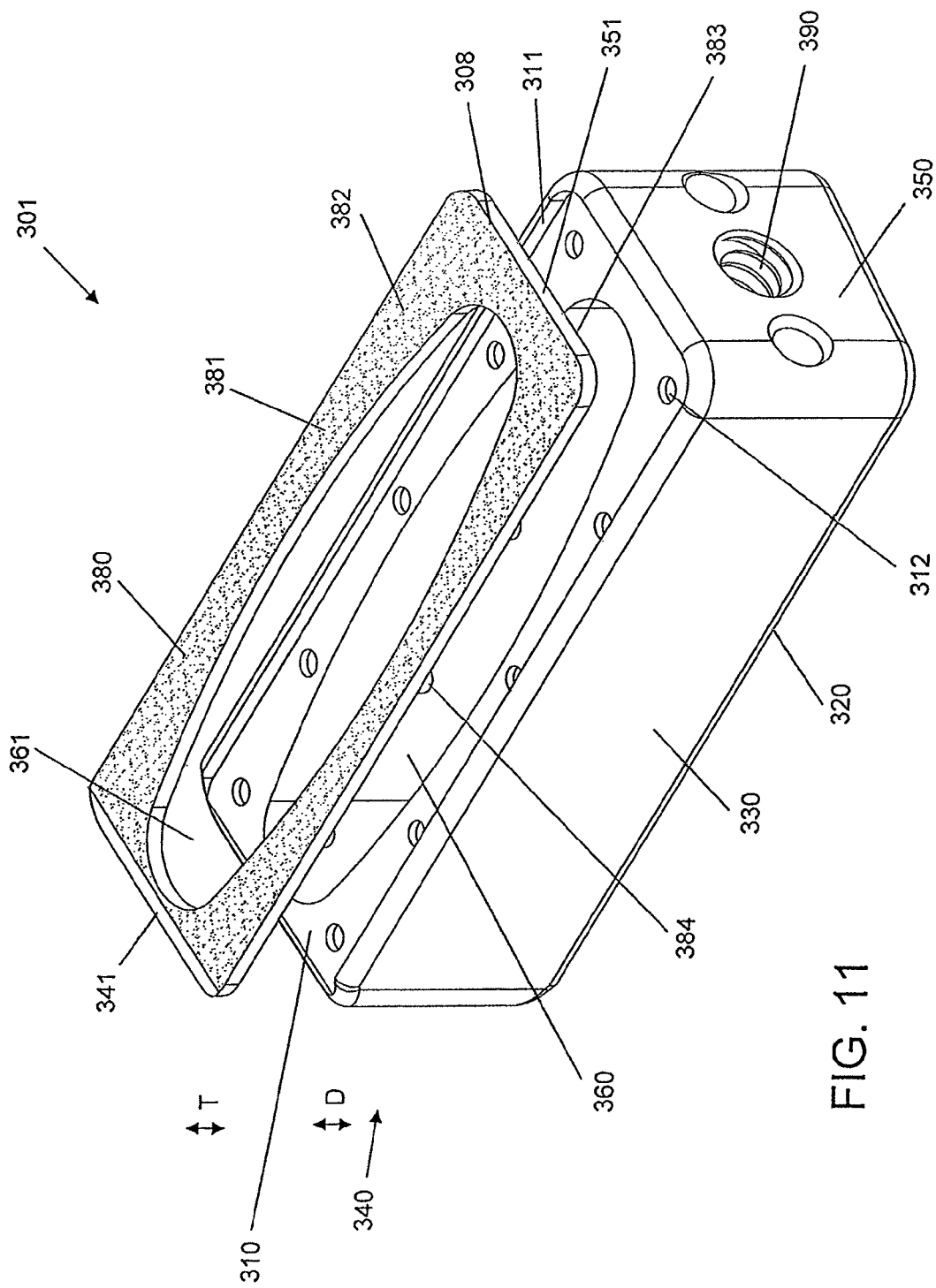
FIG. 11 shows an exploded view of a lateral lumbar implant with an integration plate.

In some aspects, the implant 1, 101, 101a, and 201 includes an integration plate 82, 182, 182a, and 282, for example, as shown in FIG. 8A-FIG. 10 and FIG. 12. In addition, a lateral implant 301 having a substantially rectangular shape may include an integration plate 382, for example, as shown in FIG. 11. The lateral implant 301 comprises the same general features as the implant 1, 101, 101a, and 201, including a top surface 310, a bottom surface 320, lateral sides 330, opposing anterior 340 and posterior 350 portions, an opening 390, as well as at least one vertical aperture 360 that extends the entire height of the implant body, and one or more transverse apertures 370 that extend the entire transverse length of the implant body.

The integration plate, shown in the drawings as component 82 (FIG. 8A and FIG. 8B), 182 (FIG. 10), 182a (FIG. 9), 382 (FIG. 11), and 282 (FIG. 12), respectively, includes the roughened surface topography 80, 180, 180a, 280, and 380, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body of the implant 1, 101, 101a, 201, and 301, respectively, and the posterior portion 51, 151, 151a, 251, and 351 aligns with the posterior portion 50, 150, 150a, 250, and 350 of the main body of the implant 1, 101, 101a, 201, and 301, respectively. The vertical aperture 61, 161, 161a, 261, and 361 preferably aligns with the vertical aperture 60, 160, 160a, 260, and 360 of the main body of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The top surface 81, 181, 181a, 281, and 381 of the integration plate 82, 182, 182a, 282, and 382 preferably comprises the roughened topography 80, 180, 180a, 280, and 380. The bottom surface 83, 183, 183a, 283, and 383 of the integration plate 82, 182, 182a, 282, and 382 preferably comprises a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body of the implant 1, 101, 101a, 201, and 301, respectively, and thus facilitate the connection between the integration plate 82, 182, 182a, 282, and 382 and the main body of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient to which the implant 1, 101, 101a, 201, and 301 is to be implanted. Among these different sizes, shapes, and features are lordotic angles; anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

Figure 8A:
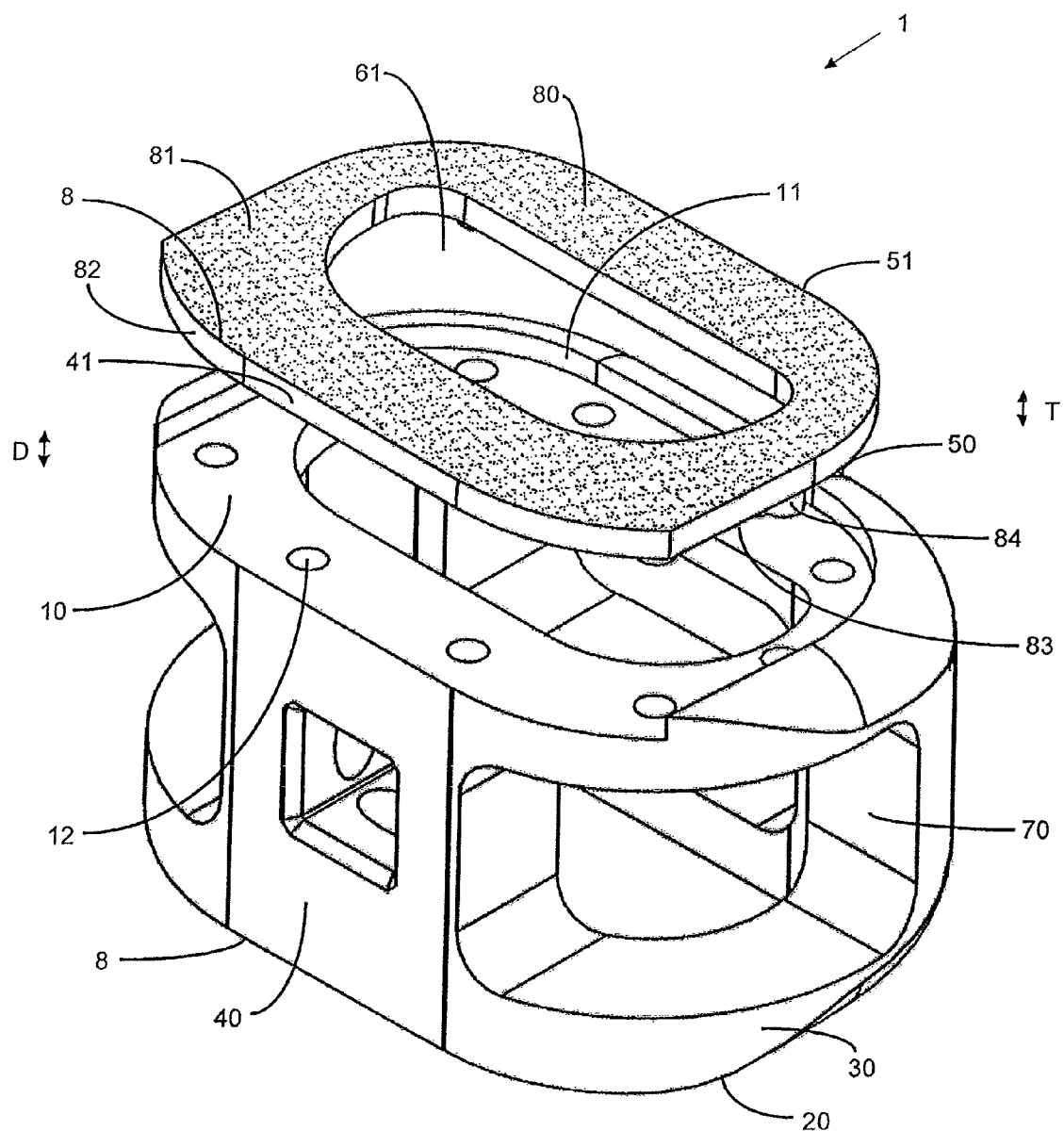
FIG. 8A shows an exploded view of a generally oval-shaped implant with an integration plate.
Figure 8B:
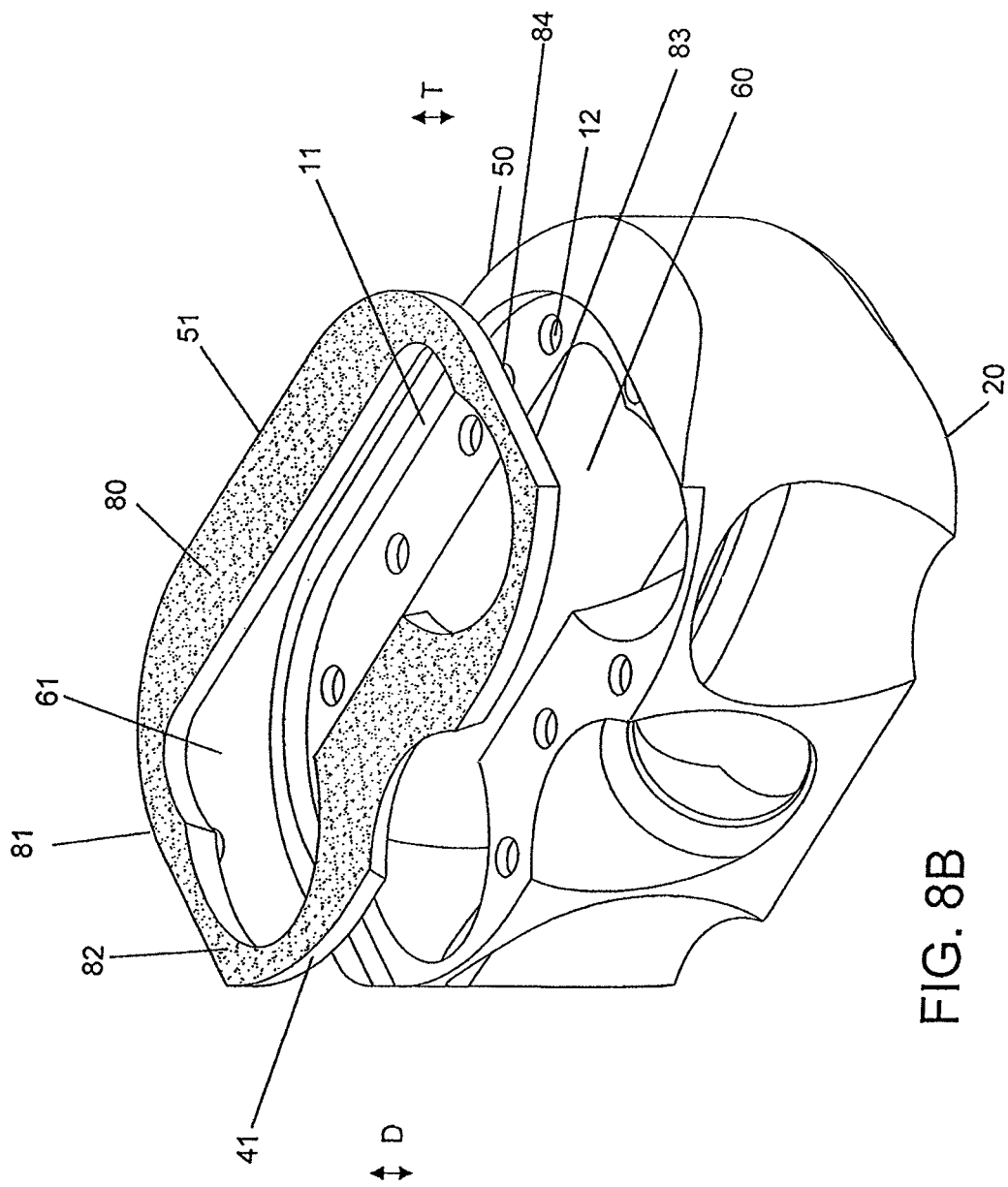
FIG. 8B shows an exploded view of a generally oval-shaped implant with integration fixation and an integration plate.
Figure 12:
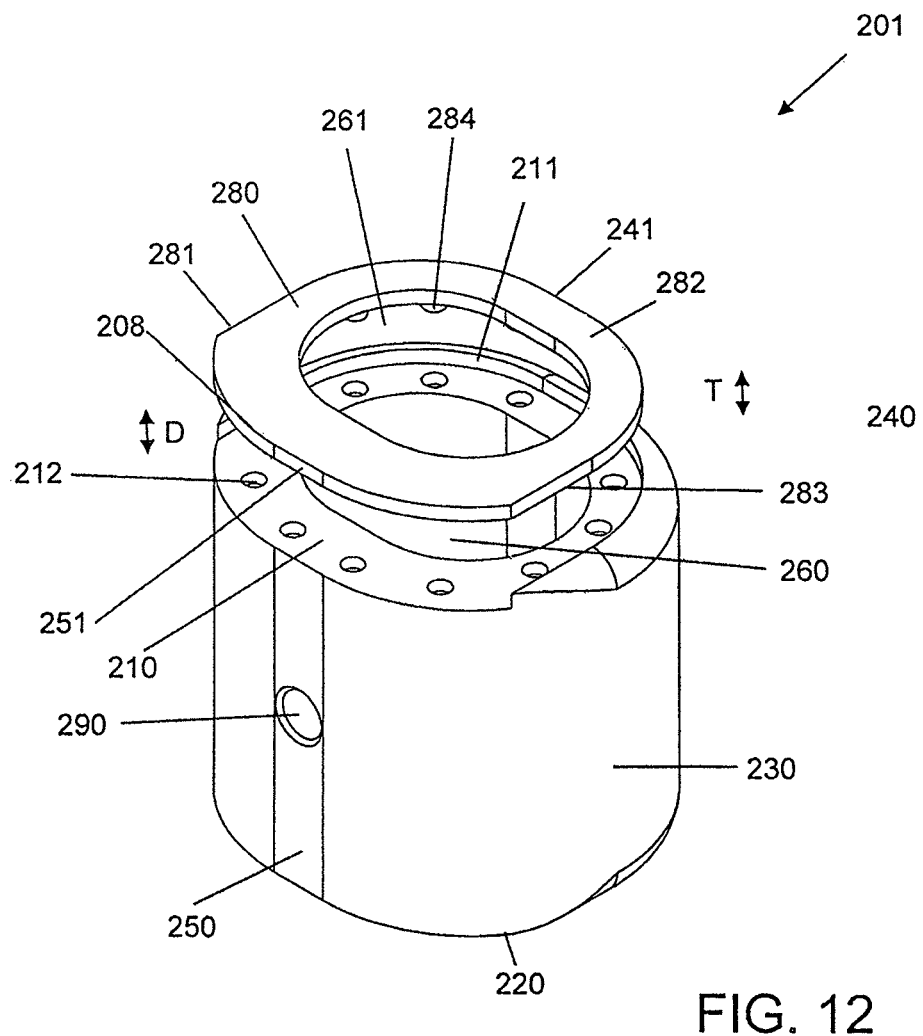
FIG. 12 shows an exploded view of a generally oval-shaped anterior cervical implant with an integration plate.

FIG. 8A and FIG. 8B show that the top surface 10 is recessed and comprises a plurality of holes 12, but the recessed bottom surface 20 and its holes 12 are not shown. FIG. 9 shows that the top surface 110a is recessed and comprises a plurality of holes 112a, but the recessed bottom surface 120a and its holes 112a are not shown. FIG. 10 shows that the top surface 110 is recessed and comprises a plurality of holes 112, but the recessed bottom surface 120 and its holes 112 are not shown. FIG. 11 shows that the top surface 310 is recessed and comprises a plurality of holes 312, but the recessed bottom surface 320 and its holes 312 are not shown. FIG. 12 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

Figure 13A:
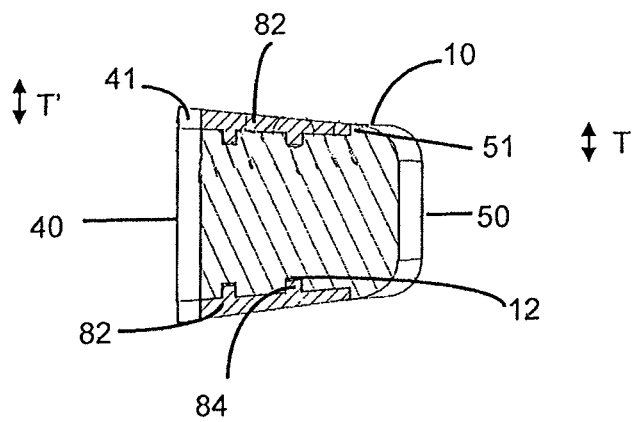
FIG. 13A shows a cut-away view of an integration plate.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 120, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness T of the posterior portion 51, 151, 151a, 251, and 351. For example, as shown in FIG. 13A, the anterior portion 41 has a greater thickness T' than the thickness T of the posterior portion 51.

The recess depth D, the thickness T, and the thickness T' may each independently be from about 0.1 mm to about 10 mm. In preferred aspects, the recess depth D, the thickness T, and the thickness T' may each independently be from about 1 mm to about 5 mm. Thus, for example, either the recess depth D, the thickness T, and the thickness T' may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341, posterior portion 51, 151, 151a, 251, and 251 or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382). The integration plate 82, 182, 182a, 282, and 382 is preferably metal, and may be used with a metal implant. The metal integration plate 82, 182, 182a, 282, and 382 may also be used with a molded plastic or polymer implant, or a composite implant. In some aspects, the integration plate 82, 182, 182a, 282, and 382 may also comprise a plastic, polymeric, or composite material.

Figure 13B:
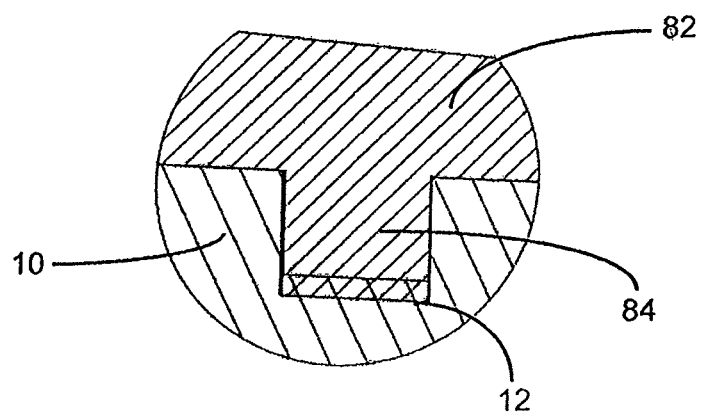
FIG. 13B shows a close-up of the cut-away portion illustrated in FIG. 13A with the post of the integration plate fit within a hole in the implant top surface.

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184a, 284, and 384 and the hole 12, 112, 112a, 212, and 312 may comprise a friction fit. For example, FIG. 13A shows a cut-away side view of the implant 1 having an integration plate 82 on the top 10 and bottom 20 portions, with the posts 84 inserted into the holes 12. FIG. 13B shows a close up view of the post 84 and hole 12 connection. In some aspects, the reciprocal connector such as the post 84, 184, 184a, 284, and 384 and the connector of the body such as the hole 12, 112, 112a, 212, and 312 have additional compatible structures and features to further strengthen the connection between the integration plate 82, 182, 182a, 282, and 382 and the implant 1, 101, 101a, 201, and 301. Non-limiting examples of such structures and features are illustrated in FIGS. 14-17.

The structures and features may be on either or both of the integration plate 82, 182, 182a, 282, and 382 and the main body of the implant 1, 101, 101a, 201, and 301. In general, the structures include fasteners, compatibly shaped joints, compatibly shaped undercuts, and/or other suitable connectors having different shapes, sizes, and configurations. For example, a fastener may include a pin, screw, bolt, rod, anchor, snap, clasp, clip, clamp, or rivet. In some aspects, an adhesive may be used to further strengthen any of the integration plate 82, 182, 182a, 282, and 382 and implant 1, 101, 101a, 201, and 301 connections described in this specification. An adhesive may comprise a cement, glue, polymer, epoxy, solder, weld, or other suitable binding material.

Figures 14A, 14B:
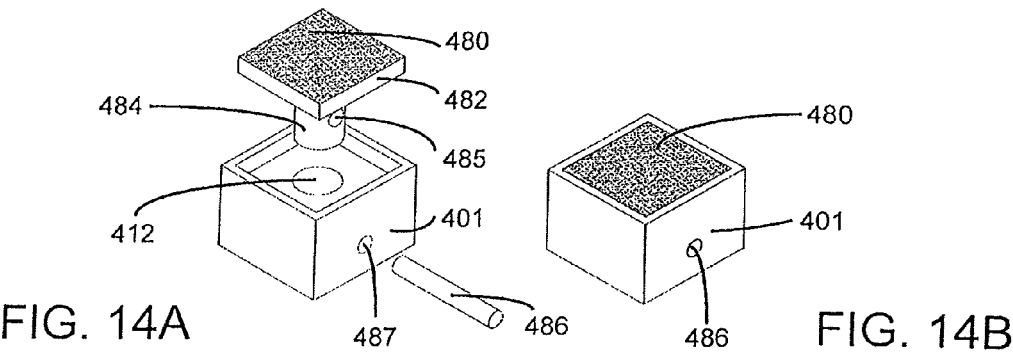
FIG. 14A shows an exploded view of a pin connection suitable for mounting an integration plate onto an implant.
FIG. 14B shows the pin connection illustrated in FIG. 14A with the components assembled.
Figure 14C:
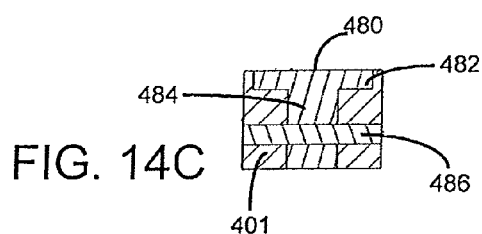
FIG. 14C shows a cut-away view of the pin connection illustrated in FIGS. 14A and 14B.

As shown in FIGS. 14A-14C, an integration plate 482 (shown in the drawings as a box only for illustration purposes) having a roughened surface topography 480 may comprise one or more reciprocal connectors such as one or more posts 484 each having a bore 485 extending through a horizontal plane. The post 484 is inserted into a connector such as a hole 412 through the implant 401 (also shown in the drawings as a box only for illustration purposes). A fastener 486, which may be a pin 486, is inserted through the bore 485 (FIG. 14A), thereby preventing the post 484 from being disengaged from the hole 412 (FIG. 14B). In some aspects, the pin 486 is also threaded through a second bore 487 that passes through the walls of the implant 401 itself, although it is preferable that the implant 401 does not include a second bore 487 through its walls and that the bore 485 is accessible from the space inside of the implant 401. It is to be understood that components numbered in the four hundred series are shown for illustration purposes, and correspond to features of each implant 1, 101, 101a, 201, and 301; for example, post 484 is representative of post 84, 184, 184a, 284, and 384.

Figures 14D, 14E:
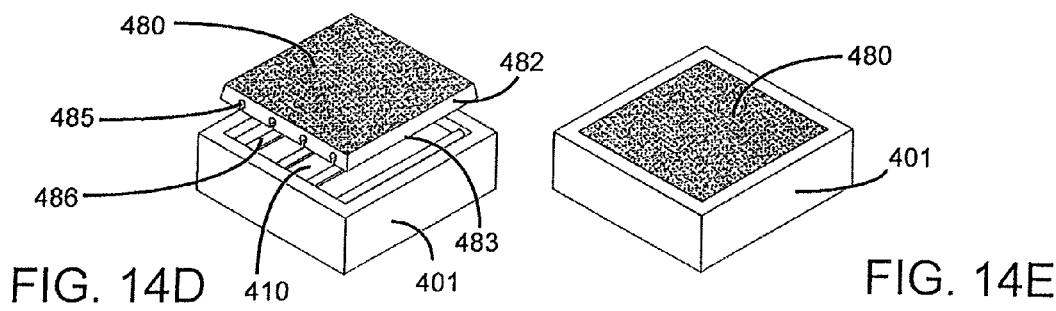
FIG. 14D shows an exploded view of a molded connection suitable for mounting an integration plate onto an implant.
FIG. 14E shows the molded connection illustrated in FIG. 14D with the components assembled.
Figure 14F:
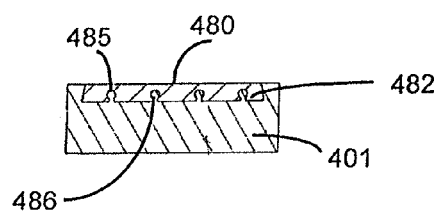
FIG. 14F shows a cut-away view of the molded connection illustrated in FIGS. 14D and 14E.

FIGS. 14D-F show another embodiment of the integration plate 482 comprising a plurality of bores 485 present on and having an opening accessible from the bottom surface 483 of the integration plate 482. The bores 485 mate with a plurality of fasteners 486, which may comprise rods 486 (FIG. 14D) integral with or otherwise attached to the top surface 410 or bottom surface (not shown) of the implant 401. For example, the rods 486 may be molded as upward-facing extensions of the top surface 410 (FIG. 14F). The rods 486 may be snap-fit into the bores 485 through the opening (FIG. 14F), in which case the opening may be slightly smaller in width than the bores 485 and rods 486, though still allowing the rods 486 to pass through the opening and into the bores 485.

In some embodiments, such as those shown in FIGS. 14G-I, the integration plate 482 comprises one or more bores 485 in a vertical plane, extending through the integration plate 482, through which a fastener 486, which may be a screw or bolt 486, may be inserted. The screw or bolt 486 may extend into a hole 412 extending at least partially into the implant 401, and the hole 412 and screw or bolt 486 preferably comprise compatible screw threads 415 (FIG. 14I). Tightening of the screw or bolt 486 secures the integration plate 482 in place on the implant 401 (FIG. 14H). In some aspects, for example, where the implant 401 is comprised of a plastic or polymeric material, the hole 412 may not be present, and the screw or bolt 486 may be screwed directly into the plastic or polymeric material, with the screw threads tightly gripping the plastic or polymeric material to form the connection. The integration plate may have a roughened topography 480.

The bottom surface 483 of the integration plate 482 may comprise undercuts in shapes that form a tight junction with compatible shapes on the implant 401. For example, as shown in FIGS. 14J-L, the bottom surface 483 may comprise a dovetail joint, or bevel, or taper that fits with a counterpart dovetail joint, bevel, or taper on the implant 401 (FIG. 14L). The shape of each of the integration plate 482 undercuts (FIG. 14I) and counterpart undercuts on the implant 401 (FIG. 14L) are such that the connection forms a joint between the implant 401 and integration plate 482, and that this joint is established and retained with a tight tolerance (FIG. 14K).

Figure 14M:
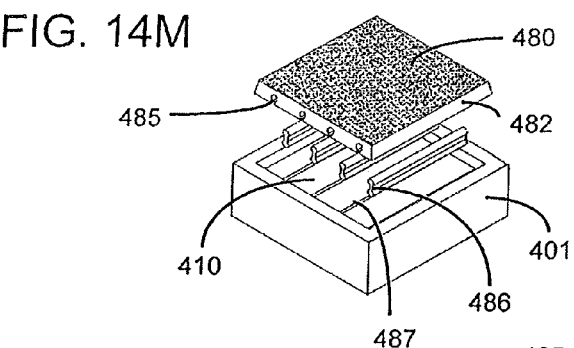
FIG. 14M shows an exploded view of adhesive-undercut connection suitable for mounting an integration plate onto an implant.
Figure 14N:
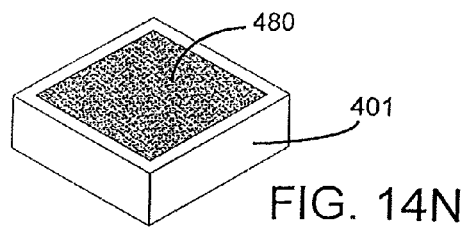
FIG. 14N shows the adhesive-undercut connection illustrated in FIG. 14M with the components assembled.
Figure 14O:
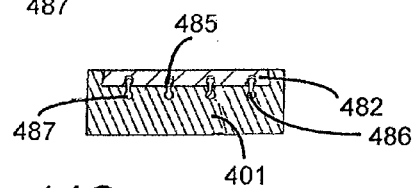
FIG. 14O shows a cut-away view of the adhesive-undercut connection illustrated in FIGS. 14M and 14N.

As shown in FIGS. 14M-O, the integration plate 482 comprising a plurality of bores 485 present on and having an opening accessible from the bottom surface 483 of the integration plate 482 may mate with a plurality of fasteners 486, which may comprise rod-shaped adhesives 486, or which may comprise rods 486 coated or otherwise impregnated with an adhesive (FIG. 14M). A rod-shaped adhesive 486 may comprise an hourglass-shaped cross section, with one side capable of being snap-fit into the bores 485 through the opening, and with the other side capable of being snap-fit into bores 487 in the top surface 410 of the implant 401. In this manner, the rod-shaped adhesive 486 may bridge the implant 401 and integration plate 482 together as shown in FIG. 14O. In an alternative embodiment, the implant 401 comprises rods 486 integral with or otherwise attached to the top surface 410 or bottom surface (not shown) of the implant 401, for example, as illustrated in FIG. 14D, and these rods 486 may be coated with an adhesive that joins the rods 486 together with the sidewalls of the bores 485 in the integration plate 482.

Figure 14P:
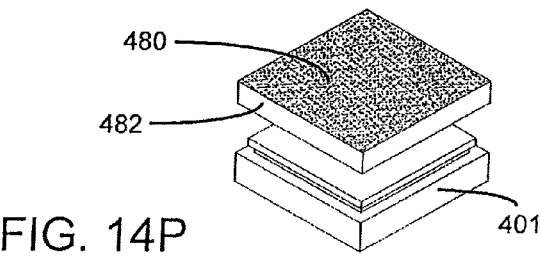
FIG. 14P shows an exploded view of a press-fit connection suitable for mounting an integration plate onto an implant.
Figure 14Q:
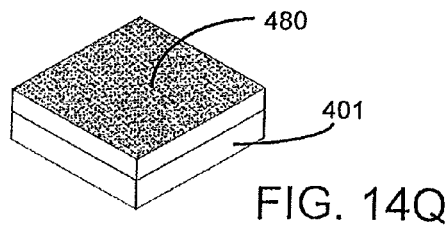
FIG. 14Q shows the press-fit connection illustrated in FIG. 14P with the components assembled.
Figure 14R:
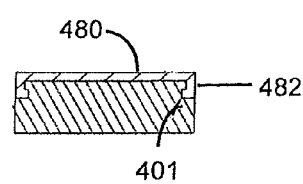
FIG. 14R shows a cut-away view of the press-fit connection illustrated in FIGS. 14P and 14Q.

An adhesive may directly join the integration plate 482 and the implant 401 together. For example, the adhesive may be applied to the bottom surface 483 of the integration plate 482 or the top surface 410 of the implant 401, and each part bridged together with the adhesive (not illustrated). In some aspects, the bottom surface 483 of the integration plate 482 may include undercuts in shapes that form a tight junction with compatible shapes on the implant 401. For example, an adhesive may be applied to undercuts and joints as shown in FIG. 14I to strengthen the connection between the integration plate 482 and the implant 401. FIGS. 14P-R show an alternative embodiment of undercuts on the integration plate 482 that form a connection with corresponding cuts on the implant 401, and an adhesive may be applied to strengthen this connection.

The integration plate 482 may be connected to the implant 401 with a snap-fit connection, for example, as shown in FIGS. 14S-U. The integration plate 482 may comprise one or more bores 485 extending vertically through the integration plate 482, through which a fastener 486, which may be a rivet, snap or snap button 486, may be inserted (FIG. 14S). The rivets 486, snaps 486, or snap buttons 486 may be integral with or otherwise attached to the top surface 410 (FIG. 14S) or bottom surface (not shown) of the implant 401. For example, the rivets 486, snaps 486, or snap buttons 486 may be molded as upward-facing extensions of the top surface 410 (FIG. 14U). In some preferred aspects, the rivets 486, snaps 486, or snap buttons 486 comprise a head portion with a diameter slightly larger than and a shaft portion with a diameter slightly smaller than the diameter of the bores 485. In some preferred aspects, at least the head portion of the rivets 486, snaps 486, or snap buttons 486 is fabricated of a material that allows the head portion to compress slightly and pass through the bores 485 when the integration plate 482 is pressed toward the implant 401, after which the head portion re-expands such that the rivets 486, snaps 486, or snap buttons 486 cannot be disengaged from the bores 485 (FIG. 14T).

In some embodiments, an anchor plate 486 enhances the connection between the posts 484 of the integration plate 482 and the holes 412 of the implant 401, as shown in FIGS. 14V-14X. For example, the top surface 410 of the implant 401 may be molded in a shape or configuration into which an anchor plate 486 may be inserted (FIG. 14X), or the anchor plate 486 may otherwise be adhered to the implant 401. The anchor plate 486 may comprise one or more bores 485 through which the post 484 may pass through (FIG. 14V). The integration plate 482, anchor plate 486, and implant 401 may be pressed together to form a tight junction that maintains the connection of the integration plate 482 to the implant 401.

The foregoing describes various non-limiting examples of how an integration plate 82, 182, 182a, 282, and 382 may be joined together with an implant 1, 101, 101a, 201, and 301. One non-limiting objective of this approach is to provide a roughened topography 80, 180, 180a, 280, and 380 to the surface of the implant 1, 101, 101a, 201, and 301. The roughened topography 80, 180, 180a, 280, and 380 can be established on the integration plate 82, 182, 182a, 282, and 382 according to any suitable methodology, including those described or exemplified in this specification. The roughened topography 80, 180, 180a, 280, and 380 may also be provided by coating the implant 1, 101, 101a, 201, and 301 or the integration plate 82, 182, 182a, 282, and 382 with a roughened topography material (e.g., FIGS. 15A-F).

For example, in some aspects, a material such as metal filings, shavings, or fine metal particles or powder, or fine plastic or polymeric particles may be laid onto the top surface 10, 110, 110a, 210, and 310 or bottom surface 20, 120, 120a, 220, and 320 of the implant 1, 101, 101a, 201, and 301 or onto the top surface 81, 181, 181a, 281, and 381 of the integration plate 82, 182, 182a, 282, and 382 according to any suitable method. In some aspects, an adhesive may be used to affix the material to the implant 1, 101, 101a, 201, and 301 or integration plate 82, 182, 182a, 282, and 382. Plastic or polymeric materials may be spray-coated, airlaid, or melt-blown onto the implant 1, 101, 101a, 201, and 301 or integration plate 82, 182, 182a, 282, and 382. The materials may be adhered directly, for example, by at least partially melting the particles such that they fuse to the desired surface when they cool. Metal materials may be cold sprayed or thermal sprayed onto the implant 1, 101, 101a, 201, and 301 or integration plate 82, 182, 182a, 282, and 382 according to any suitable technique.

FIGS. 15A-C show a non-limiting embodiment of a roughened topography 480 coated onto the top surface 410 of the implant 401 (shown in the drawings as a box only for illustration purposes). The roughened topography 480 may also be coated onto the bottom surface of the implant 401 (not shown). The roughened topography 480 may be coated onto the top surface 481 of the integration plate 482 (not shown).

In some alternative aspects, a backing 479 comprising a roughened topography 480 may be laid onto the top surface 410 of the implant 401 as shown in FIGS. 15D-F. For example, the backing 479 may comprise a foil, mesh, screen, or other suitable material, preferably comprising a metal, that is sufficiently flexible such that it may conform to the shapes and contours of the top surface 410 of the implant 401 (FIG. 15E and FIG. 15F). In this same manner, the backing 479 may be laid onto the top surface 481 of the integration plate 482 (not shown). An adhesive may be used to join the backing 479 to the top surface 410 of the implant 401 or top surface 481 of the integration plate 482. The backing 479 may be soldered, melted, or welded to the top surface 410 of the implant 401 or top surface 481 of the integration plate 482.

A preferred connection between the integration plate 82, 182, 182a, 282, and 382 and the implant 1, 101, 101a, 201, and 301 includes the post 84, 184, 184a, 284, and 384 and hole 12, 112, 112a, 212, and 312 connection, without additional fasteners required to maintain this connection, for example, through a friction fit. In some embodiments the post 84, 184, 184a, 284, and 384 and hole 12, 112, 112a, 212, and 312 include different interlocking joints to strengthen the connection between them. These interlocking joints preferably include different configurations of a basic tongue-and-groove joint, for example, as shown in FIGS. 16 and 17.

Figure 16A:
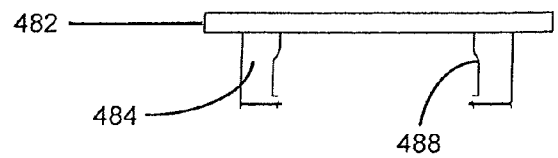
FIG. 16A shows a side view of the representation of an integration plate having posts with one groove for mating with a corresponding tongue structure in an implant hole.
Figure 16B:
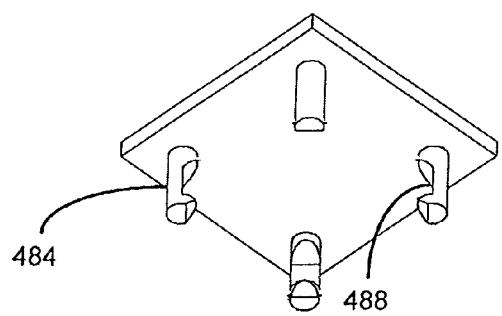
FIG. 16B shows a bottom view of the representation illustrated in FIG. 16A.
Figure 16C:
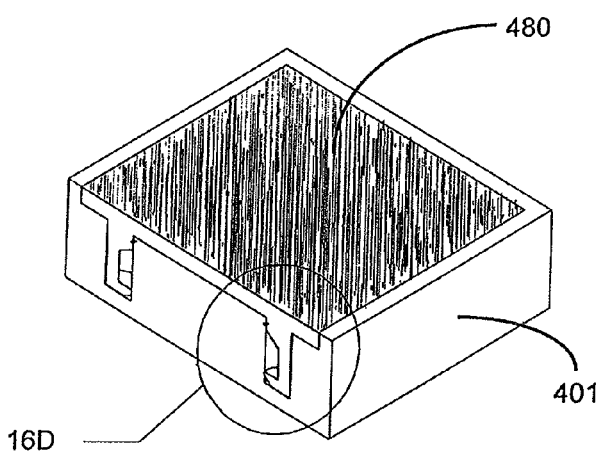
FIG. 16C shows an example of a tongue-and-groove connection suitable for mounting an integration plate onto an implant.
Figure 16D:
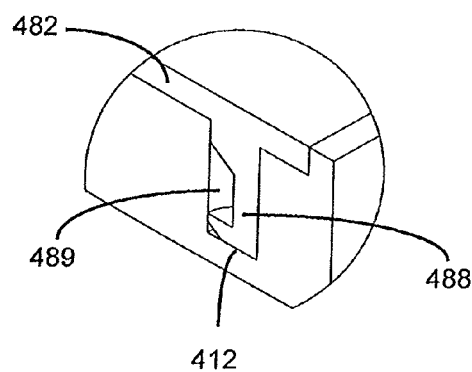
FIG. 16D shows a close-up view of the tongue-and-groove connection illustrated in FIG. 16C.
Figure 16E:
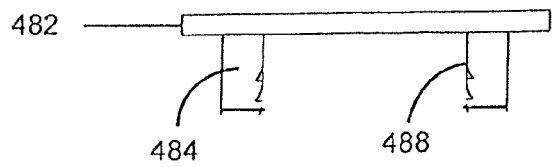
FIG. 16E shows a side view of a representation of an integration plate having posts with three grooves for mating with a corresponding tongue structure in an implant hole.
Figure 16F:
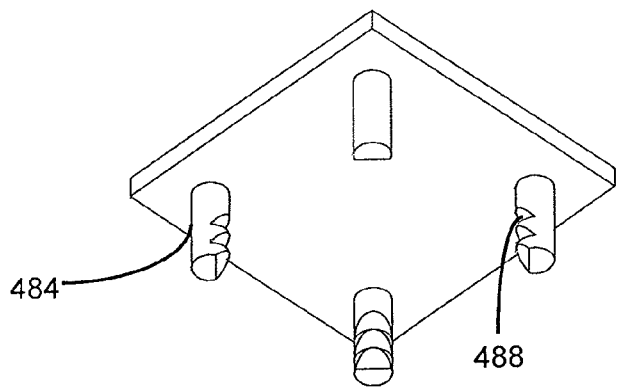
FIG. 16F shows a bottom view of the representation illustrated in FIG. 16E.

In some embodiments, an integration plate 482 (shown in the drawings as a box only for illustration purposes) having a roughened surface topography 480 may comprise one or more posts 484 (FIG. 16A), each comprising a groove 488 (FIG. 16A and FIG. 16B). The posts 484 may include more than one groove 488, including two, three, four, five, six, seven, eight or more grooves 488. FIG. 16E and FIG. 16F show a non-limiting example of a post 484 with three groves 488.

Figure 16G:
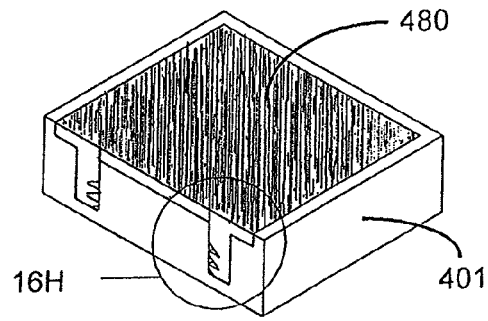
FIG. 16G shows an example of a multiple tongue-and-groove connection suitable for mounting an integration plate onto an implant.
Figure 16H:
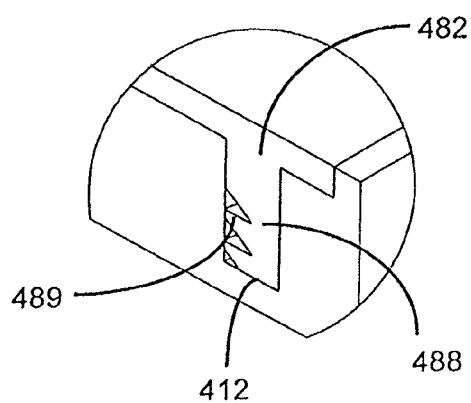
FIG. 16H shows a close-up view of the multiple tongue-and-groove connection illustrated in FIG. 16G.

Each groove 488 preferably mates with a corresponding tongue 489 in the hole 412 of the implant 401. For example, as shown in FIGS. 16C and 16D, each hole 412 may include one tongue 489 that forms a connection with one groove 488 in the post 484. The holes 412 may include more than one tongue 489, including two, three, four, five, six, seven, eight or more tongues 489. FIGS. 16G and 16H show a non-limiting example of each hole 412 including three tongues 489.

When the integration plate 482 is pressed together with the implant 401 (shown in the drawings as a box only for illustration purposes), the post 484 is inserted into its corresponding hole 412, and each tongue 489 is inserted into its corresponding groove 488. In this regard, it is preferable that the material used to fabricate the tongue 489 is sufficiently flexible to allow the wider portions of the post 484 that flank each groove 488 to pass over the tongue 489 so that the tongue 489 can fit within its groove 488, yet is sufficiently rigid to prevent disengagement of the tongue 489 from the groove 488 once the integration plate 482 and implant 481 are together.

Figure 16I:
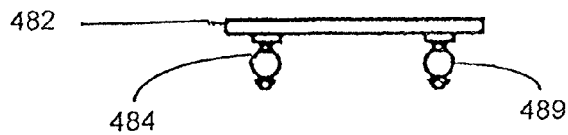
FIG. 16I shows a side view of a representation of an integration plate having posts with a rounded tongue structure for mating with a corresponding groove in an implant hole.
Figure 16J:
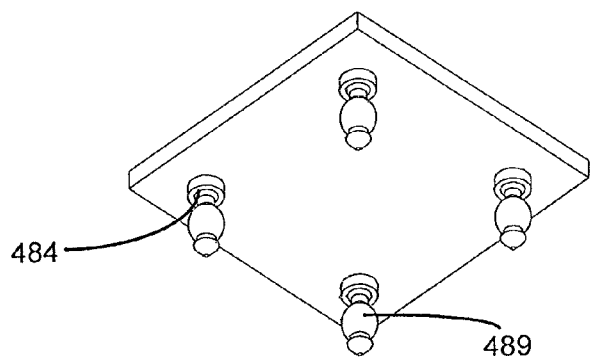
FIG. 16J shows a bottom view of the representation illustrated in FIG. 16I.

In some embodiments, the location of the tongue 489 and groove 488 on the post 484 and hole 412 are reversed. For example, the tongue 489 may be present on the post 484 and the groove 488 may be present on the hole 412. FIGS. 16I-X show examples of a post 484 and hole 412 connection in which the post 484 comprises one or more tongues 489 that fit within one or more grooves 488 in the sidewalls of the hole 412.

Figure 16K:
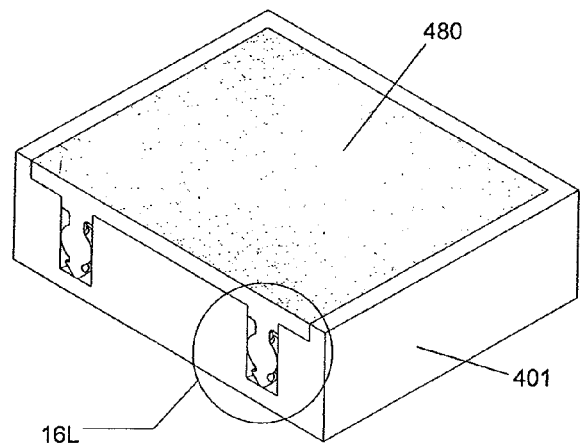
FIG. 16K shows an example of a rounded tongue-and-groove connection suitable for mounting an integration plate onto an implant.
Figure 16L:
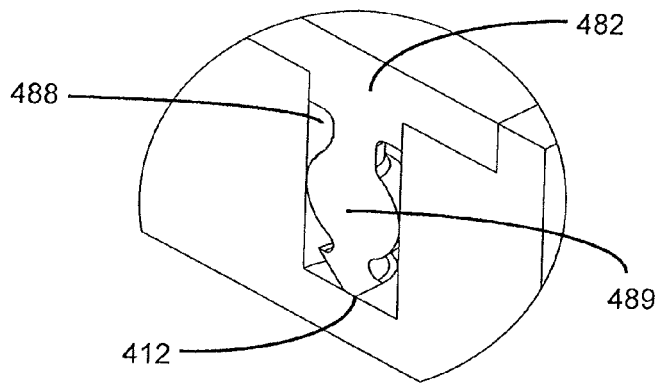
FIG. 16L shows a close-up view of the rounded tongue-and-groove connection illustrated in FIG. 16K.
Figure 16M:
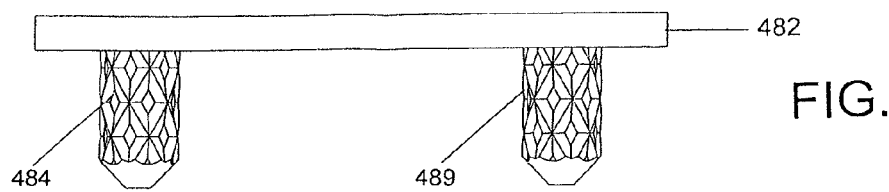
FIG. 16M shows a side view of a representation of an integration plate having posts with a diamond-shaped tongue structure for mating with a corresponding diamond-shaped groove in an implant hole.
Figure 16N:
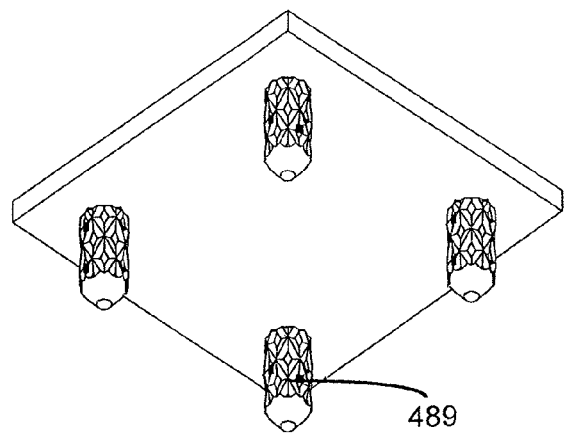
FIG. 16N shows a bottom view of the representation illustrated in FIG. 16M.
Figure 16O:
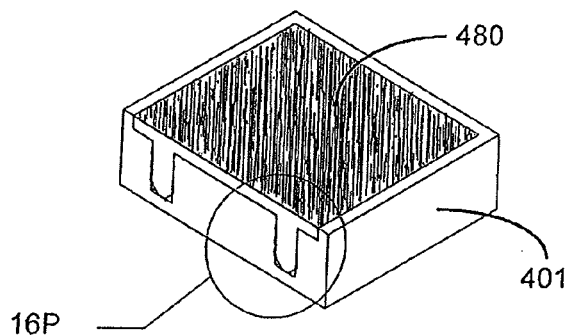
FIG. 16O shows an example of a diamond-shaped tongue-and-groove connection suitable for mounting an integration plate onto an implant.
Figure 16P:
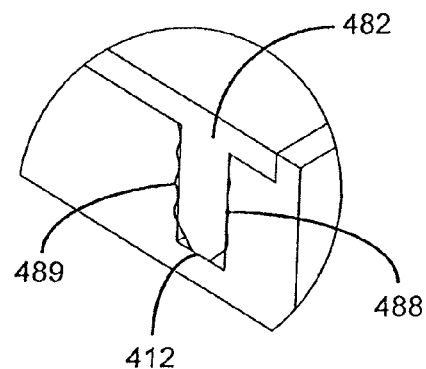
FIG. 16P shows a close-up view of the diamond-shaped tongue-and-groove connection illustrated in FIG. 16O.
Figure 16Q:
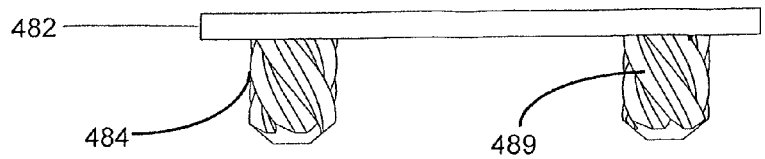
FIG. 16Q shows a side view of a representation of an integration plate having posts with a threaded tongue structure for mating with a corresponding threaded groove in an implant hole.
Figure 16R:
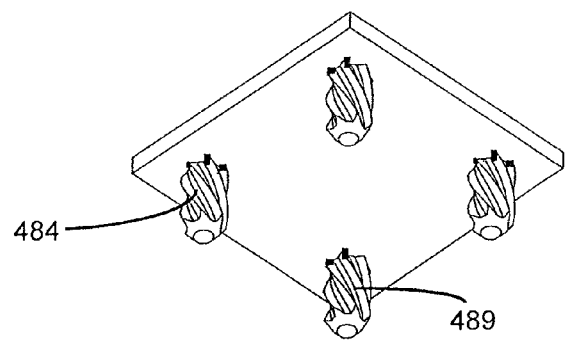
FIG. 16R shows a bottom view of the representation illustrated in FIG. 16Q.
Figure 16S:
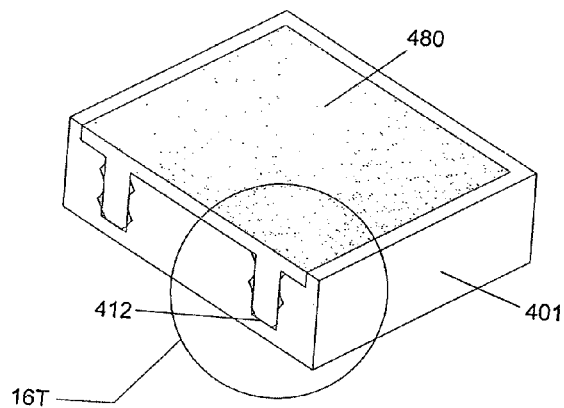
FIG. 16S shows an example of a threaded tongue-and-groove connection suitable for mounting an integration plate onto an implant.
Figure 16T:
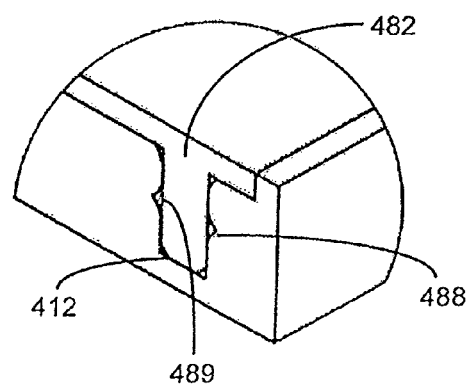
FIG. 16T shows a close-up view of the threaded tongue-and-groove connection illustrated in FIG. 16S.
Figure 16U:
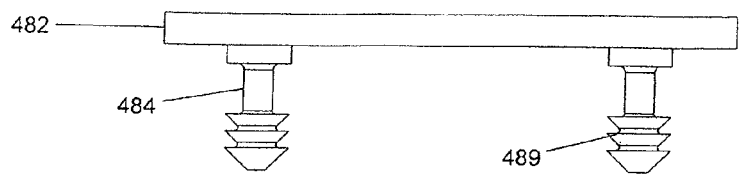
FIG. 16U shows a side view of a representation of an integration plate having posts with a plurality of a disc-shaped structures for mating with corresponding grooves in an implant hole.
Figure 16V:
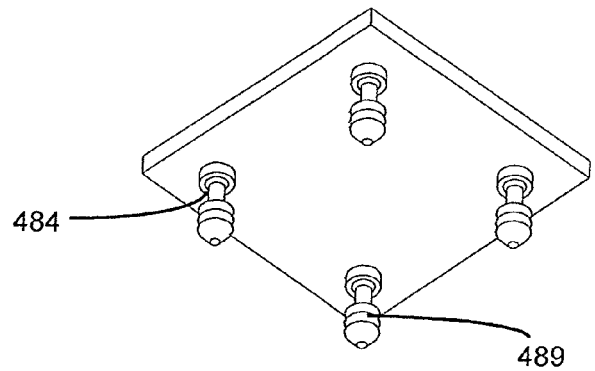
FIG. 16V shows a bottom view of the representation illustrated in FIG. 16U.
Figure 16W:
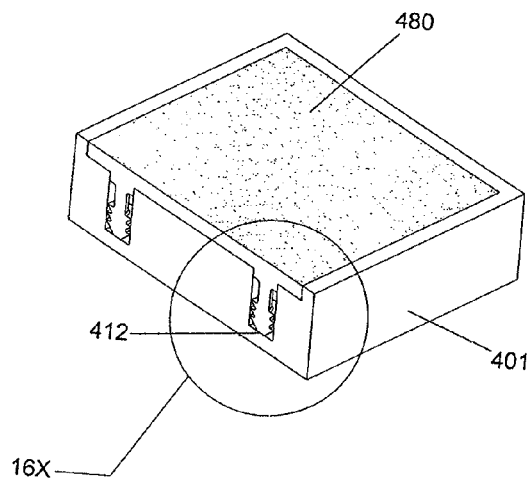
FIG. 16W shows an example of a disc-shaped tongue and groove connection suitable for mounting an integration plate onto an implant.
Figure 16X:
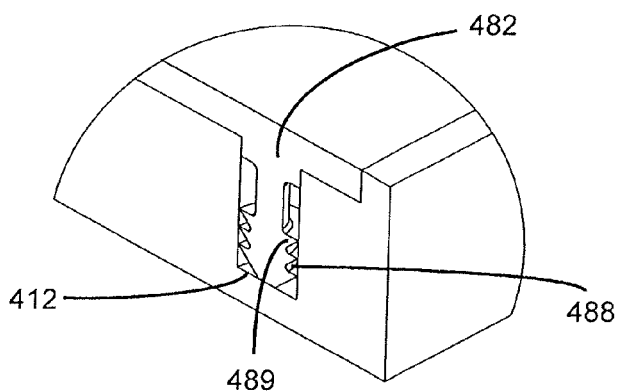
FIG. 16X shows a close-up view of the disc-shaped tongue and groove connection illustrated in FIG. 16W.
Figure 16Y:
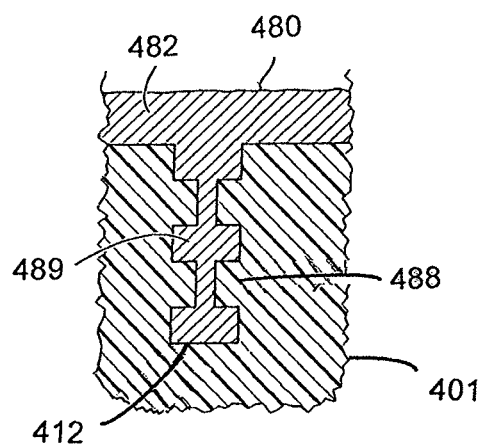
FIG. 16Y shows a cut-away view of the disc-shaped tongue and groove connection illustrated in FIGS. 16W and 16X.
Figure 17A:
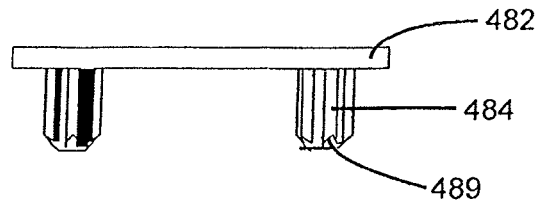
FIG. 17A shows a side view of a representation of an integration plate having posts with vertically-oriented star-shaped tongue-and-groove structures for mating with corresponding vertically-oriented tongue-and-groove structures in an implant hole.
Figure 17B:
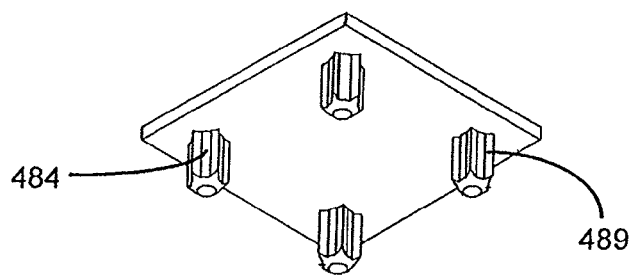
FIG. 17B shows a bottom view of the representation illustrated in FIG. 17A.
Figure 17C:
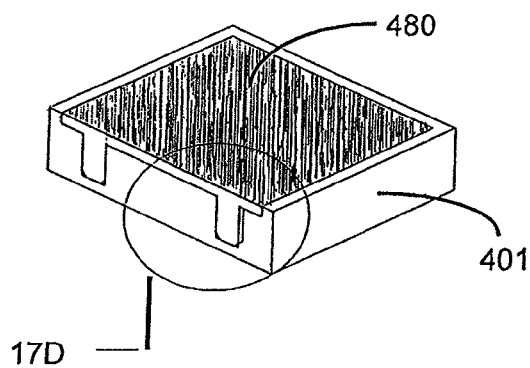
FIG. 17C shows an example of a star-shaped tongue-and-groove connection suitable for mounting an integration plate onto an implant.
Figure 17D:
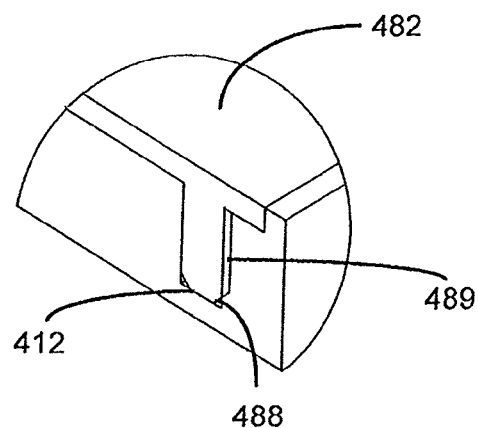
FIG. 17D shows a close-up view of the star-shaped tongue-and-groove connection illustrated in FIG. 17C.

The tongue 489 may comprise a round shape (FIGS. 16I and 16I), and may thus mate with a groove 488 having a reciprocal round shape (FIGS. 16K and 16L). The tongue 489 may comprise a triangular shape (FIGS. 16E and 16F), and may thus mate with a groove 488 having a reciprocal triangular shape (FIGS. 16G and 16H). The tongue 489 may comprise a diamond shape (FIGS. 16M and 16N), and may thus mate with a groove 488 having a reciprocal diamond shape (FIGS. 16O and 16P). The tongue 489 may comprise a threaded shape (FIGS. 16Q and 16R), and may thus mate with a groove 488 having a reciprocal threaded shape (FIGS. 16S and 16T). The tongue 489 may comprise a disc shape (FIGS. 16U and 16V), and may thus mate with a groove 488 having a reciprocal disc shape (FIGS. 16W and 16X). A cross-section of such a configuration is shown in FIG. 16Y.

Each hole may include one groove 488 that forms a connection with one tongue 489 on the post 484. The holes 412 may include more than one groove 488, including two, three, four, five, six, seven or more grooves 488. The post 484 may include more than one tongue 489, including two, three, four, five, six, seven, eight or more tongues 489.

When the integration plate 482 is pressed together with the implant 401, the post 484 is inserted into its corresponding hole 412, and the tongue 489 is inserted into its corresponding groove 488. It is preferable that the material out of which the tongue 489 is fabricated is sufficiently flexible to allow the tongue 489 to pass over the wider portions of the hole 412 that flank each groove 488 so that the tongue 489 can fit within its groove 488, yet is sufficiently rigid to prevent disengagement of the tongue 489 from the groove 488 once the integration plate 482 and implant 481 are together.

Whether on the post 484 or the hole 412, the tongue 489 and groove 488 may comprise any suitable shape, and preferably, each has a shape compatible with its counterpart. The shape may be regular or irregular. Each of the tongue 489 and groove 488 may comprise a substantially round, triangular, diamond, square, dovetail, or polygonal shape. Optionally, an adhesive may be used to further strengthen the connection between the tongue 489 and the groove 488.

FIGS. 16A-Y show non-limiting examples of a tongue 489 and groove 488 connection in which each tongue 489 and groove 488 are oriented in a horizontal plane. In some aspects, the tongue 489 and groove 488 may be oriented in a vertical plane. For example, as shown in FIGS. 17A-D, an integration plate 482 may comprise one or more posts 484, with each post 484 comprising one or more vertically oriented tongues 489. Each vertically oriented tongue 489 preferably mates with a corresponding vertically oriented groove 488 in the hole 412. The posts 484 may, for example, have a star shape (FIGS. 17A and 17B) with the edges of the stars forming both tongues 489 and grooves 488, and the holes 412 may have a reciprocal star shape (FIGS. 17C and 17D) with the edges of the stars forming reciprocal grooves 488 and tongues 489.

When the integration plate 482 is pressed together with the implant 401 (shown in the drawings as a box only for illustration purposes), the post 484 is inserted into its corresponding hole 412, and the vertically oriented tongue 489 is inserted into its corresponding vertically oriented groove 488. Each post 484, including its vertically oriented tongues 489, preferably has a wider diameter than the corresponding hole 412, including the vertically oriented grooves 488, such that a tight friction fit is established and maintained between the post 484 and the hole 412. Optionally, an adhesive may be used to further strengthen the connection.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant is to be seated near the center of the vertebral endplate or the implant is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101*a*, 201, and 301 include smooth, rounded, and highly radiused posterior portions and lateral sides which may minimize extraneous bone removal for endplate preparation and reduce localized stress concentrations. Thus, interbody surgical implant 1, 101, 101*a*, 201, and 301 and methods of using it are particularly useful in preserving the natural arch of the vertebral endplate and minimizing the chance of implant subsidence.

Because the endplates are spared during the process of inserting the spinal implant 1, 101, 101*a*, 201, and 301, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Interbody spinal implant 1 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, those embodiments having a surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1 may provide secure seating and prove difficult to remove. Thus, certain embodiments of the interbody spinal implant 1, 101, 101*a*, 201, and 301 may maintain a position between the vertebral endplates due, at least in part, to resultant annular tension attributable to press-fit surgical implantation and, post-operatively, improved osteointegration at the top surface 10, 110, 110*a*, 210, and 310; the bottom surface 20, 120, 120*a*, 220, and 320; or both surfaces.

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101*a*, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101*a*, 201, and 301 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

Embodiments of the invention allow end-plate preparation with custom-designed rasps. These rasps preferably have a geometry matched with the geometry of the implant. The rasps conveniently remove cartilage from the endplates and remove minimal bone, only in the postero-lateral regions of the vertebral end-plates. It has been reported in the literature that the end-plate is the strongest in postero-lateral regions.

After desired annulotomy and discectomy, embodiments of the invention first adequately distract the disc space by inserting (through impaction) and removing sequentially larger sizes of very smooth distractors, which have been size matched with the size of the available implant 1. Once adequate distraction is achieved, the surgeon prepares the end-plate with a rasp. There is no secondary instrumentation required to keep the disc space distracted while the implant 1, 101, 101*a*, 201, and 301 is inserted, as the implant 1, 101, 101*a*, 201, and 301 has sufficient mechanical strength that it is impacted into the disc space. In fact, the height of the implant 1, 101, 101*a*, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101*a*, 201, and 301 is designed such that all the impact loads are applied only to the titanium part of the construct. Thus, the implant 1, 101, 101*a*, 201, and 301 has adequate strength to allow impact. The sides of the implant 1, 101, 101*a*, 201, and 301 have smooth surfaces to allow for easy implantation and, specifically, to prevent binding of the implant 1, 101, 101*a*, 201, and 301 to soft tissues during implantation.

The invention encompasses a number of different implant 1, 101, 101*a*, 201, and 301 configurations, including a one-piece, titanium-only implant and a composite implant formed of top and bottom plates (components) made out of titanium. The surfaces exposed to the vertebral body are dual acid etched to allow for bony in-growth over time, and to provide resistance against expulsion. The top and bottom titanium plates are assembled together with the implant body that is injection molded with PEEK. The net result is a composite implant that has engineered stiffness for its clinical application. The axial load is borne by the PEEK component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101*a*, 201, and 301 designed according to certain embodiments allows the vertebral end-plate to deflect and allows healing of the bone graft into fusion.

The roughened topography 80, 180, 180*a*, 280, and 380 whether directly on the top/bottom surface of the implant 1, 101, 101*a*, 201, and 301 or the integration plate 82, 182, 182*a*, 282, and 382 reacts with contacting bone to promote biologic activities that facilitate fusion of bone to the implant 1, 101, 101*a*, 201, and 301. The implant 1, 101, 101*a*, 201, and 301 is configured to resist movement after being seated in the joint space of the spine. To enhance movement resistance and provide additional stability under spinal loads in the body, the implant 1, 101, 101*a*, 201, and 301 may comprise one or more anti-expulsion edges 8, 108, 108*a*, 208, and 308 that tend to "dig" into the end-plates slightly and help to resist expulsion (FIGS. 18A-18M). The anti-expulsion edges 8, 108, 108*a*, 208, and 308 may be present on the top surface 10, 110, 110*a*, 210, and 310; the bottom surface 20, 120, 120*a*, 220, and 320; or both surfaces of the implant 1, 101, 101*a*, 201, and 301.

By way of example, FIG. 18A shows an anti-expulsion edge 8 on the top surface 10 and bottom surface 20 of the anterior face 40 of the implant 1. Each anti-expulsion edge 8 protrudes above the plane of the top surface 10 and bottom surface 20, with the amount of protrusion increasing toward the anterior face 40 and the highest protrusion height P at the anterior-most edge of the top surface 10 or bottom surface 20. As shown in FIG. 18B, the protruding anti-expulsion edge 8 exposes a protruding surface 9.

An anti-expulsion edge 8, 108, 108*a*, 208, and 308 may be oriented toward the anterior portion 40, 140, 140*a*, 240, and 340, or the posterior portion 50, 150, 150*a*, 250, and 350, or either of the opposing lateral sides 30, 130, 130*a*, 230, and 330. The orientation of the anti-expulsion edge 8, 108, 108*a*, 208, and 308 may depend on the intended orientation of the implant 1, 101, 101*a*, 201, and 301 when it has been implanted between vertebrae in the patient.

Figure 18I:
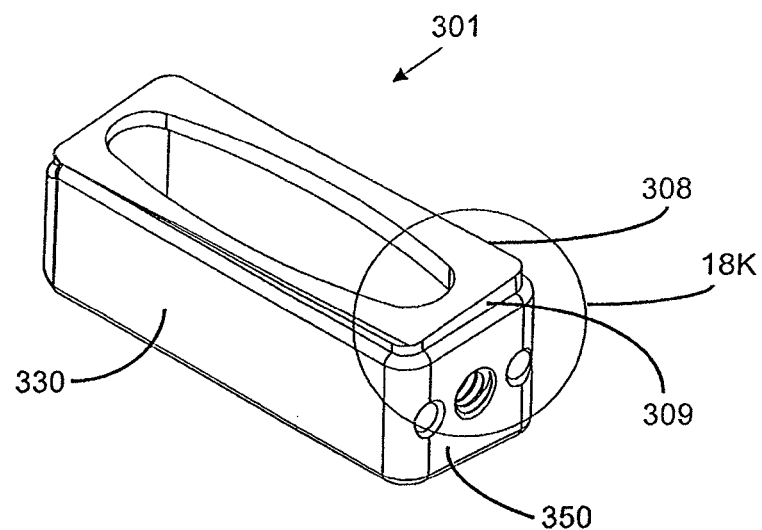
FIG. 18I shows a perspective view of a rectangular-shaped implant with a protruding anti-expulsion edge oriented toward one of the lateral sides.
Figure 18J:
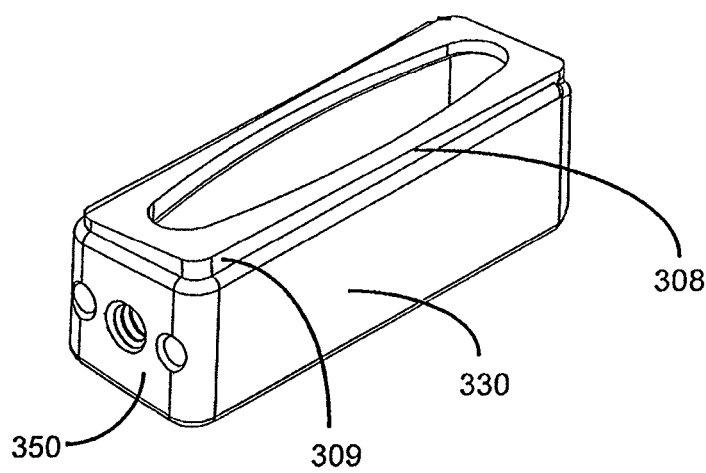
FIG. 18J shows another perspective view of the implant illustrated in FIG. 18I.
Figure 18K:
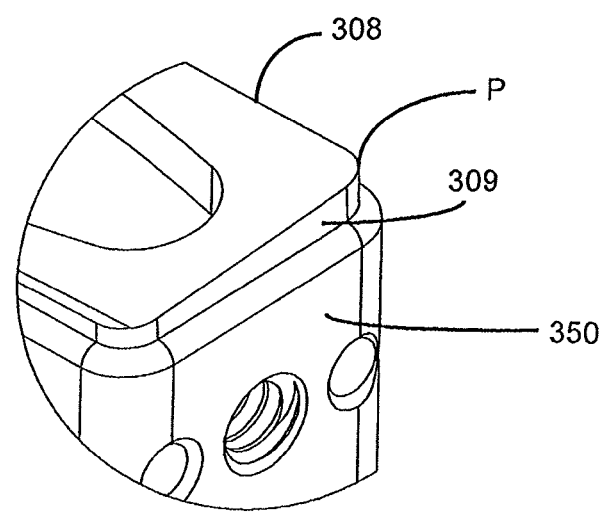
FIG. 18K shows a close-up view of the protruding anti-expulsion edge of the implant illustrated in FIG. 18I.
Figure 18L:
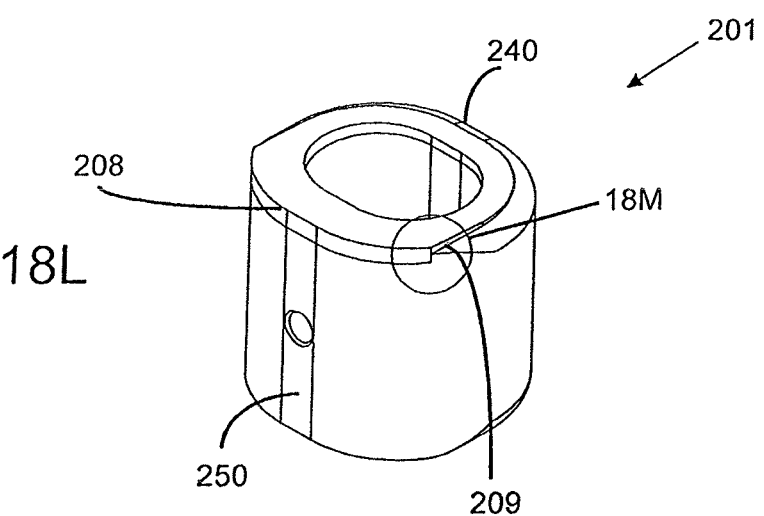
FIG. 18L shows a perspective view of a cervical implant with a protruding anti-expulsion edge.
Figure 18M:
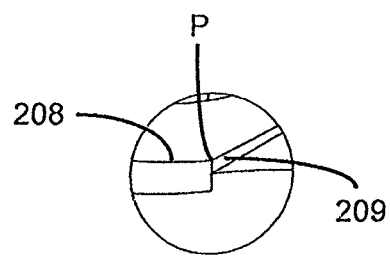
FIG. 18M shows a close-up view of the protruding anti-expulsion edge of the implant illustrated in FIG. 18L.

FIGS. 18C-18H show different perspective views of different embodiments of the implant 101 and 101*a*, with the amount of protrusion increasing toward the posterior face 150 and 150*a* and the highest protrusion height P at the posterior-most edge of the top surface 110 and 110*a* or bottom surface 120 and 120*a*. The protruding anti-expulsion edge 108 and 108*a* exposes a protruding surface 109 and 109*a*. FIGS. 18I-18K show different perspective views of an embodiment of the implant 301, with the amount of protrusion increasing toward one of the opposing lateral sides 330 and the highest protrusion height P at the most lateral edge of the top surface 310 or bottom surface 320. The protruding anti-expulsion edge 308 exposes a protruding surface 309. FIGS. 18L and 18M show different perspective views of an embodiment of the implant 201, with the amount of protrusion increasing toward the anterior portion 240 and the highest protrusion height P at the anterior-most edge of the top surface 210 or bottom surface 220. The protruding anti-expulsion edge 208 exposes a protruding surface 209.

In some preferred embodiments, the integration plate 82, 182, 182*a*, 282, and 382 establishes the anti-expulsion edge 8, 108, 108*a*, 208, and 308 for either or both of the top surface 10, 110, 110*a*, 210, and 310 and bottom surface 20, 120, 120*a*, 220, and 320 of the implant 1, 101, 101*a*, 201, and 301. Different integration plates 82, 182, 182*a*, 282, and 382 may be used to establish a range of highest protrusion heights P.

Figure 19A:
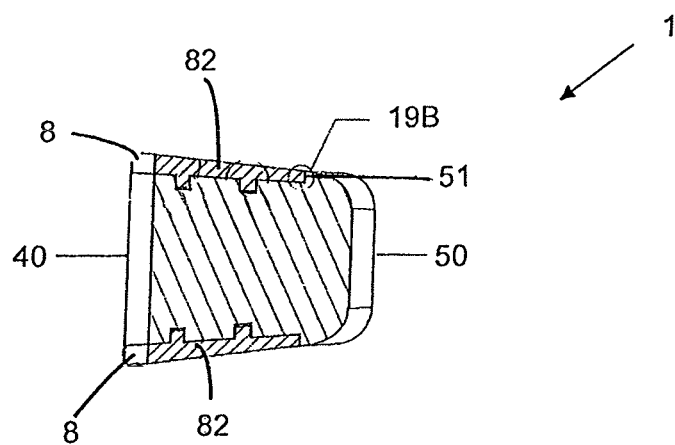
FIG. 19A shows a cut-away view of an implant with an integration plate having a protruding anti-expulsion edge.
Figure 19B:
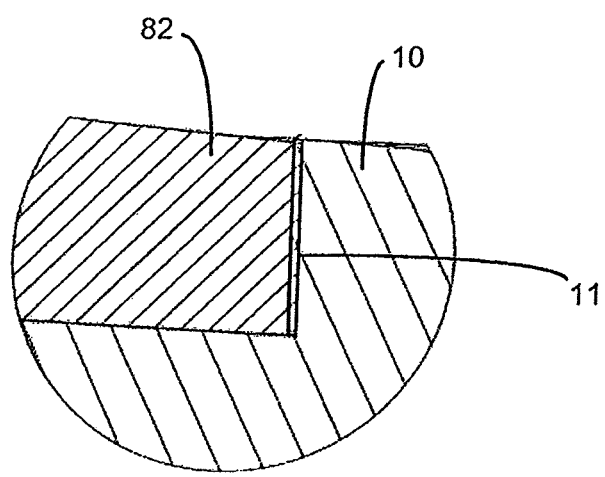
FIG. 19B shows a smooth joint between the integration plate and the implant illustrated in FIG. 19A.

When an integration plate 82 is used, it is preferred that the posterior portion 51 is substantially flush with the posterior portion edges of the implant 1, for example, by having a thickness equivalent to the recess depth D. In other words, it is preferred that the junction of the posterior portion 51 of the integration plate 82 with the implant 1 not protrude higher than the plane of the top surface 10 or bottom surface 20 of the implant 1. FIG. 19A shows a cross-section of the implant 1 with an integration plate 82 having a protruding anti-expulsion edge 8, and FIG. 19B shows a close-up of the joint of the integration plate 82 and the top surface 10 of the implant 1.

Figure 20A:
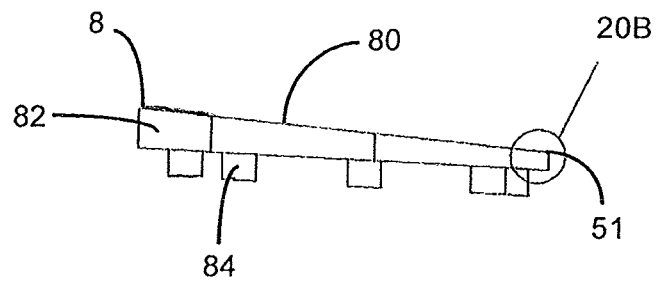
FIG. 20A shows a side view of an integration plate having a protruding anti-expulsion edge.
Figure 20B:
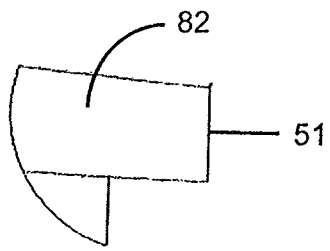
FIG. 20B shows a sharp edge configuration of the posterior edge of the integration plate illustrated in FIG. 20A.
Figure 20C:
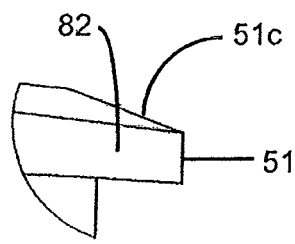
FIG. 20C shows a chamfered edge configuration of the posterior edge of an integration plate.
Figure 20D:
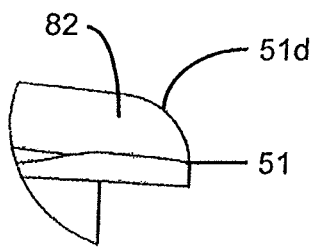
FIG. 20D shows a radiused edge configuration of the posterior edge of an integration plate.

The posterior portion 51 of the integration plate 82 may comprise different edge features. FIGS. 20A-D show non-limiting examples of possible configurations of the posterior portion 51 of the integration plate 82, with FIGS. 20B-D showing an enlarged view of the posterior portion 51 as encircled in FIG. 20A. For example, the posterior portion 51 may have a substantially straight edge as shown in FIG. 20A and FIG. 20B, such that the edge of the posterior portion 51 aligns with a corresponding straight edge in the posterior portion 50 of the implant 1. In some alternative aspects, the posterior portion 51 may have a substantially straight edge, and include a beveled edge or chamfer 51C as shown in FIG. 20C. In some alternative aspects, the posterior portion 51 may have a generally blunt nosed profile, including a generally rounded profile 51D as shown in FIG. 20D.

The implant 1, 101, 101*a*, 201, and 301 may comprise a lordotic angle L, e.g., may be wedge-shaped to facilitate sagittal alignment. Thus, for example, the anterior portion 40, 140, 140*a*, 240, and 340 of the implant 1, 101, 101*a*, 201, and 301 may comprise a height that is larger than the height of the posterior portion 50, 150, 150*a*, 250, and 350. The lordotic angle L may be established by the implant 1, 101, 101*a*, 201, and 301 itself, or may be established by the integration plate 82, 182, 182*a*, 282, and 382 when combined with the implant 1, 101, 101*a*, 201, and 301.

Figure 21:
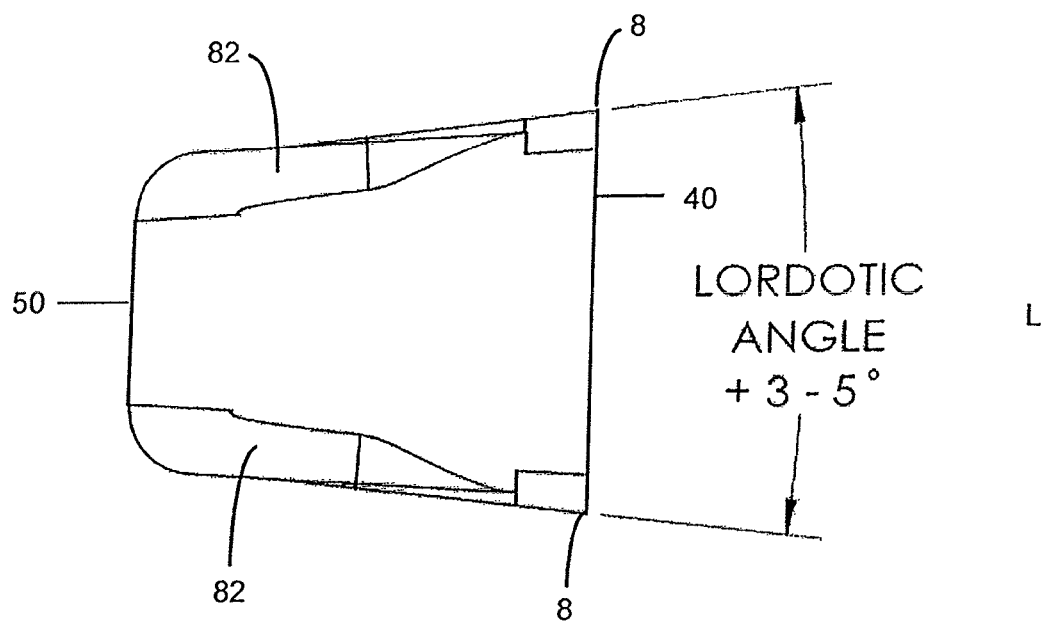
FIG. 21 shows an example of an integration plate lordotic angle.

The lordotic angle L of the implant 1 preferably closely approximates, or otherwise is substantially the same as, the angle of lordosis of the spine of the patient where the implant 1, 101, 101*a*, 201, and 301 will be implanted. In some aspects, the integration plate 82, 182, 182*a*, 282, and 382 increases the lordotic angle L by about 3% to about 5%, measured according to the angle of lordosis of a particular patient's spine. For example, as shown in FIG. 21, the anti-expulsion edge 8 protrudes to a height sufficient to increase the overall height H of the anterior portion 40 of the implant 1 such that implant 1 has a lordotic angle L that is about 3% to about 5% greater than the patient's angle of lordosis.

The implant 1, 101, 101*a*, 201, and 301 may have a lordotic angle L about 3%, about 3.3%, about 3.5%, about 3.7%, about 4%, about 4.3%, about 4.5%, about 4.7%, or about 5% greater than the patient's angle of lordosis, though percentages greater than 5% or lesser 3% are possible. The increase of about 3% to about 5% preferably results from the combination of the protruding height of the integration plate 82, 182, 182*a*, 282, and 382 on the top portion 10, 110, 110*a*, 210, and 310 and bottom portion 20, 120, 120*a*, 220, and 320 of the implant 1, 101, 101*a*, 201, and 301.

Figure 22:
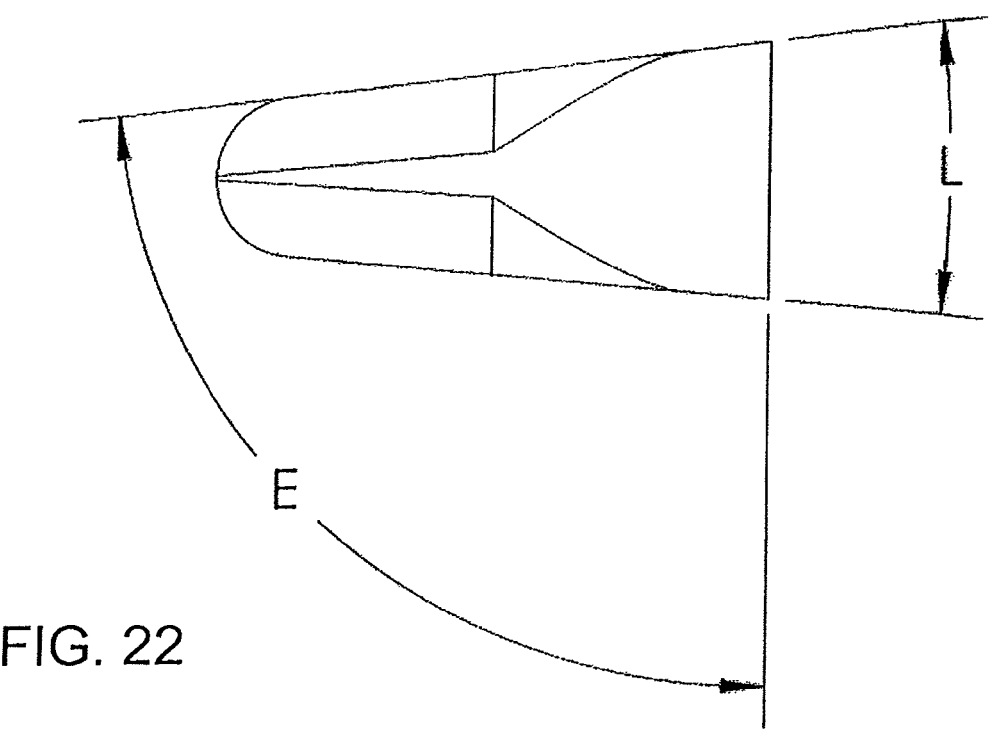
FIG. 22 shows a example of an anti-expulsion edge angle.

The expulsion-resistant edge 8, 108, 108*a*, 208, and 308 may comprise an anti-expulsion edge angle E, for example, as shown in FIG. 22 with respect to the implant 1. The anti-expulsion edge angle E may be from about 80 degrees to about 100 degrees. In preferred aspects, the anti-expulsion edge angle E may be measured by taking into account the lordosis angle L of the implant 1, 101, 101*a*, 201, and 301. In highly preferred aspects, the anti-expulsion edge angle E is measured by subtracting half of the lordotic angle L from 90 degrees. For example, where the lordosis angle L of the implant 1, 101, 101a, 201, and 301 is 12 degrees, the anti-expulsion edge angle E is 84 degrees (90−(12×0.5)). The anti-expulsion edge angle E may be about 80 degrees, about 81 degrees, about 82 degrees, about 83 degrees, about 84 degrees, about 85 degrees, about 86 degrees, about 86.5 degrees, about 87 degrees, about 88 degrees, or about 89 degrees.

The top and bottom surfaces of the implant may be made out of titanium and are dual acid etched. The dual acid etching process creates a highly roughened texture on these surfaces, which generates tremendous resistance to expulsion. The width of these dual acid etched surfaces is very broad and creates a large area of contact with the vertebral end-plates, further increasing the resistance to expulsion.

The implant 1 according to certain embodiments of the invention has a large foot-print, and offers several sizes. Because there is no secondary instrument required to maintain distraction during implantation, all the medial-lateral (ML) exposure is available as implantable ML width of the implant. This feature allows the implant to contact the vertebral end-plates at the peripheral apophyseal rim, where the end-plates are the strongest and least likely to subside.

Further, there are no teeth on the top and bottom surfaces (teeth can create stress risers in the end-plate, encouraging subsidence). Except for certain faces, all the implant surfaces have heavily rounded edges, creating a low stress contact with the end-plates. The wide rim of the top and bottom surfaces, in contact with the end-plates, creates a low-stress contact due to the large surface area. Finally, the implant construct has an engineered stiffness to minimize the stiffness mismatch with the vertebral body which it contacts.

The implant 1 according to certain embodiments of the invention has a large foot-print. In addition, titanium provides high strength for a small volume. In combination, the large foot-print along with the engineered use of titanium allows for a large volume of bone graft to be placed inside the implant.

It is believed that an intact vertebral end-plate deflects like a diaphragm under axial compressive loads generated due to physiologic activities. If a spinal fusion implant is inserted in the prepared disc space via a procedure which does not destroy the end-plate, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1 according to certain embodiments of the invention allows the vertebral end-plate to deflect and facilitates healing of the bone graft into fusion.

The top and bottom surfaces of the implant 1 according to certain embodiments of the invention are made of titanium and are dual acid etched. The dual acid etched surface treatment of titanium allows in-growth of bone to the surfaces. Hence, the implant 1 is designed to incorporate with the vertebral bone over time. It may be that the in-growth happens sooner than fusion. If so, there may be an opportunity for the patients treated with the implant 1 to return to normal activity levels sooner than currently recommended by standards of care.

Even the titanium-only embodiment of the invention has been designed with large windows to allow for radiographic evaluation of fusion, both through AP and lateral X-rays. A composite implant minimizes the volume of titanium, and localizes it to the top and bottom surfaces. The rest of the implant is made of PEEK which is radiolucent and allows for free radiographic visualization.

Although illustrated and described above with reference to certain specific embodiments and examples, the invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed:

1. An interbody spinal implant, comprising:
a body having a top surface, a bottom surface, opposing lateral sides, opposing anterior and posterior portions, a substantially hollow center, and a single vertical aperture extending from the top surface to the bottom surface, and having varying width and maximum width at its center, wherein a portion of the top surface of the body, and optionally the bottom surface of the body, is recessed and has a connector for affixing an integration plate to the body and the connector optionally comprises an adhesive, and wherein the non-recessed portion of the top surface and, if the bottom surface is recessed, the non-recessed portion of the bottom surface comprises a blunt and radiused portion; and
a first integration plate, and optionally a second integration plate, comprising a top surface having a roughened surface topography adapted to grip bone and inhibit migration of the implant, a bottom surface having a reciprocal connector, which optionally comprises an adhesive, for joining together with the connector of the body, opposing lateral sides, opposing anterior and posterior portions, and a single vertical aperture extending from the top surface to the bottom surface of the integration plate, aligning with the single vertical aperture of the body, and defining a transverse rim with a varying width wherein the entire bottom surface of the first integration plate is inserted into the recessed portion of the top surface of the body, and the connector and reciprocal connector are joined together, thereby affixing the first integration plate to the body, and if a second integration plate is present, the entire bottom surface of the second integration plate is inserted into the recessed portion of the bottom surface of the body, and the connector and reciprocal connector are joined together, thereby affixing the second integration plate to the body.

2. The interbody spinal implant of claim 1, wherein the connector comprises a plurality of holes, and the reciprocal connector comprises a plurality of posts inserted into the plurality of holes, and wherein the plurality of posts include a bore extending horizontally therethrough into which a pin is inserted.

3. The interbody spinal implant of claim 1, wherein the connector comprises an anchor plate having a plurality of holes, and the reciprocal connector comprises a plurality of posts inserted into the plurality of holes on the anchor plate.

4. The interbody spinal implant of claim 1, wherein the reciprocal connector comprises one or more bores in the bottom surface of the first integration plate, and the connector comprises one or more rods inserted into the one or more bores in the bottom surface of the first integration plate, and if a second integration plate is present, the reciprocal connector comprises one or more bores in the bottom surface of the second integration plate, and the connector comprises one or more rods inserted into the one or more bores in the bottom surface of the second integration plate.

5. The interbody spinal implant of claim 1, wherein the reciprocal connector comprises a plurality of vertical bores extending through the first integration plate, and the connector comprises a plurality of screws inserted into the plurality of vertical bores and into the top surface of the body or the bottom surface of the body, and if a second integration plate is present, the reciprocal connector comprises a plurality of vertical bores extending through the second integration plate, and the connector comprises a plurality of screws inserted into the plurality of vertical bores and into the top surface of the body or the bottom surface of the body.

6. The interbody spinal implant of claim 1, wherein the reciprocal connector comprises a plurality of vertical bores extending through the first integration plate, and the connector comprises a plurality of snap buttons inserted through the plurality of vertical bores, and if a second integration plate is present, the reciprocal connector comprises a plurality of vertical bores extending through the second integration plate, and the connector comprises a plurality of snap buttons inserted through the plurality of vertical bores.

7. The interbody spinal implant of claim 1, wherein the reciprocal connector and the connector each comprise compatibly shaped undercuts that form an interlocking joint when the reciprocal connector and the connector are joined together.

8. The interbody spinal implant of claim 1, wherein the body and the first integration plate are each comprised of a metal, and if a second integration plate is present, the second integration plate is comprised of a metal.

9. The interbody spinal implant of claim 1, wherein the body is comprised of a non-metal polymer and the first integration plate is comprised of a metal, and if a second integration plate is present, the second integration plate is comprised of a metal.

10. The interbody spinal implant of claim 9, wherein the non-metal polymer is selected from the group consisting of polyetherether-ketone, hedrocel, and ultra-high molecular weight polyethylene.

11. The interbody spinal implant of claim 1, wherein the body is comprised of a composite of a metal and a non-metal polymer selected from the group consisting of polyetherether-ketone, hedrocel, and ultra-high molecular weight polyethylene.

12. The interbody spinal implant of claim 1, wherein the body and the first integration plate are generally oval-shaped in transverse cross-section, and if a second integration plate is present, the second integration plate is generally oval-shaped in transverse cross-section.

13. The interbody spinal implant of claim 1, wherein the body and the first integration plate are generally rectangular-shaped in transverse cross-section, and if a second integration plate is present, the second integration plate is generally rectangular-shaped in transverse cross-section.

14. The interbody spinal implant of claim 1, wherein the body and the first integration plate are generally curved-shaped in transverse cross-section, and if a second integration plate is present, the second integration plate is generally curved-shaped in transverse cross-section.

15. The interbody spinal implant of claim 1, wherein the anterior portion of the body or the posterior portion of the body comprises an opening for achieving one or more of the following functions: being adapted to engage a delivery device, facilitating delivery of bone graft material to the substantially hollow center, enhancing visibility of the implant, and providing access to bone graft material.

16. The interbody spinal implant of claim 1, further comprising bone graft material disposed in the substantially hollow center.

17. The interbody spinal implant of claim 16, wherein the bone graft material is cancellous autograft bone, allograft bone, demineralized bone matrix (DBM), porous synthetic bone graft substitute, bone morphogenic protein (BMP), or a combination thereof.

18. The interbody spinal implant of claim 1, wherein the interbody spinal implant comprises a lordotic angle adapted to facilitate alignment of the spine.

19. The interbody spinal implant of claim 1, wherein at least one of the anterior and posterior portions of the first integration plate comprise an anti-expulsion edge to resist pullout of the implant from the spine of a patient into which the implant has been implanted, and if a second integration plate is present, at least one of the anterior and posterior portions of the second integration plate comprise an anti-expulsion edge to resist pullout of the implant from the spine of a patient into which the implant has been implanted.

20. The interbody spinal implant of claim 1, wherein the roughened surface topography comprises metal particles, metal fibers, metal powder, or combinations thereof affixed to the top surface.

21. The interbody spinal implant of claim 20, wherein the metal particles, metal fibers, metal powder, or combinations thereof are affixed to the top surface with an adhesive.

22. The interbody spinal implant of claim 20, wherein the metal particles, metal fibers, metal powder, or combinations thereof are cold sprayed onto the top surface.

23. The interbody spinal implant of claim 20, wherein the metal particles, metal fibers, metal powder, or combinations thereof are thermal sprayed onto the top surface.

24. The interbody spinal implant of claim 20, wherein the metal particles, metal fibers, metal powder, or combinations thereof are comprised on a foil backing and the foil backing is affixed to the top surface.

25. The interbody spinal implant of claim 1, wherein the body further comprises a transverse aperture.

* * * * *